United States Patent
Benson et al.

(10) Patent No.: US 12,133,797 B2
(45) Date of Patent: Nov. 5, 2024

(54) PROSTHETIC HEART VALVE DELIVERY SYSTEM: PADDLE ATTACHMENT FEATURE

(71) Applicant: 4C Medical Technologies, Inc., Maple Grove, MN (US)

(72) Inventors: Thomas Benson, Maple Grove, MN (US); Jason S. Diedering, Minneapolis, MN (US)

(73) Assignee: 4C Medical Technologies, Inc., Maple Grove, MN (US)

( * ) Notice: Subject to any disclaimer, the term of this patent is extended or adjusted under 35 U.S.C. 154(b) by 236 days.

(21) Appl. No.: 17/160,703

(22) Filed: Jan. 28, 2021

(65) Prior Publication Data
US 2021/0236274 A1   Aug. 5, 2021

Related U.S. Application Data

(60) Provisional application No. 62/968,220, filed on Jan. 31, 2020.

(51) Int. Cl.
*A61F 2/24* (2006.01)
*A61F 2/95* (2013.01)

(52) U.S. Cl.
CPC ............ *A61F 2/243* (2013.01); *A61F 2/2427* (2013.01); *A61F 2/9517* (2020.05); *A61F 2/9522* (2020.05); *A61F 2002/9505* (2013.01)

(58) Field of Classification Search
CPC ...... A61F 2/243; A61F 2/2427; A61F 2/9517; A61F 2/9522; A61F 2002/9505; A61F 2/2439; A61F 2/2418
See application file for complete search history.

(56) References Cited

U.S. PATENT DOCUMENTS

| | | | |
|---|---|---|---|
| 4,424,833 | A | 1/1984 | Spector |
| 4,503,569 | A | 3/1985 | Dotter |
| 4,733,665 | A | 3/1988 | Palmaz |
| 4,878,906 | A | 11/1989 | Lindemann |
| 5,190,528 | A | 3/1993 | Fonger |
| 5,415,667 | A | 5/1995 | Frater |

(Continued)

FOREIGN PATENT DOCUMENTS

| | | |
|---|---|---|
| AU | 2014203064 B2 | 6/2015 |
| AU | 2015230879 A1 | 10/2015 |

(Continued)

OTHER PUBLICATIONS

International Search Report and Written Opinion issued in PCT/US2021/15623, mailed Apr. 20, 2021.

(Continued)

*Primary Examiner* — Tuan V Nguyen
(74) *Attorney, Agent, or Firm* — Weiss & Arons LLP

(57) ABSTRACT

Systems, devices and methods for attaching an operator-manipulatable tether(s) to the stent for: loading and/or collapsing the expandable stent into a delivery catheter or sheath, translating the collapsed stent along the delivery catheter or sheath, delivering the expandable stent into the subject heart chamber, repositioning the expandable stent as necessary within the subject heart chamber, recapturing or resheathing the expandable stent within the delivery catheter or sheath if needed, and deploying the expandable stent to, and within, the subject heart chamber.

16 Claims, 7 Drawing Sheets

(56) References Cited

U.S. PATENT DOCUMENTS

| | | |
|---|---|---|
| 5,441,483 A | 8/1995 | Avitall |
| 5,693,083 A | 12/1997 | Baker |
| 5,693,089 A | 12/1997 | Inoue |
| 5,776,188 A | 7/1998 | Shepherd |
| 5,843,090 A | 12/1998 | Schuetz |
| 5,928,258 A | 7/1999 | Khan |
| 5,957,949 A | 9/1999 | Leonhardt |
| 5,968,070 A | 10/1999 | Bley |
| 6,123,723 A | 9/2000 | Konya |
| 6,152,144 A | 11/2000 | Lesh |
| 6,231,602 B1 | 5/2001 | Carpentier |
| 6,287,334 B1 | 9/2001 | Moll |
| 6,319,280 B1 | 11/2001 | Schoon |
| 6,319,281 B1 | 11/2001 | Patel |
| 6,332,893 B1 | 12/2001 | Mortier |
| 6,371,983 B1 | 4/2002 | Lane |
| 6,409,758 B2 | 6/2002 | Stobie |
| 6,425,916 B1 | 7/2002 | Garrison |
| 6,471,718 B1 | 10/2002 | Staehle |
| 6,494,909 B2 | 12/2002 | Greenhalgh |
| 6,503,272 B2 | 1/2003 | Duerig |
| 6,540,782 B1 | 4/2003 | Snyders |
| 6,569,196 B1 | 5/2003 | Vesely |
| 6,589,275 B1 | 7/2003 | Ivancev |
| 6,702,826 B2 | 3/2004 | Liddicoat |
| 6,738,655 B1 | 5/2004 | Sen |
| 6,790,231 B2 | 9/2004 | Liddicoat |
| 6,790,237 B2 | 9/2004 | Stinson |
| 6,821,297 B2 | 11/2004 | Snyders |
| 6,830,585 B1 | 12/2004 | Artof |
| 6,840,957 B2 | 1/2005 | Dimatteo |
| 6,875,231 B2 | 4/2005 | Anduiza |
| 7,011,671 B2 | 3/2006 | Welch |
| 7,041,132 B2 | 5/2006 | Quijano |
| 7,044,966 B2 | 5/2006 | Svanidze |
| 7,125,420 B2 | 10/2006 | Rourke |
| 7,153,324 B2 | 12/2006 | Case |
| 7,252,682 B2 | 8/2007 | Seguin |
| 7,276,077 B2 | 10/2007 | Zadno-Azizi |
| 7,276,078 B2 | 10/2007 | Spenser |
| 7,291,168 B2 | 11/2007 | Macoviak |
| 7,364,588 B2 | 4/2008 | Mathis |
| 7,381,220 B2 | 6/2008 | Macoviak |
| 7,442,204 B2 | 10/2008 | Schwammenthal |
| 7,445,631 B2 | 11/2008 | Salahieh |
| 7,455,689 B2 | 11/2008 | Johnson |
| 7,510,572 B2 | 3/2009 | Gabbay |
| 7,524,331 B2 | 4/2009 | Birdsall |
| 7,611,534 B2 | 11/2009 | Kapadia |
| 7,704,277 B2 | 4/2010 | Zakay |
| 7,749,266 B2 | 7/2010 | Forster |
| 7,758,491 B2 | 7/2010 | Buckner |
| 7,780,723 B2 | 8/2010 | Taylor |
| 7,789,909 B2 | 9/2010 | Andersen |
| 7,935,144 B2 | 5/2011 | Robin |
| 7,959,672 B2 | 6/2011 | Salahieh |
| 7,967,853 B2 | 6/2011 | Eidenschink |
| 7,998,196 B2 | 8/2011 | Mathison |
| 8,012,201 B2 | 9/2011 | Lashinski |
| 8,016,877 B2 | 9/2011 | Seguin |
| 8,021,420 B2 | 9/2011 | Dolan |
| 8,029,556 B2 | 10/2011 | Rowe |
| D648,854 S | 11/2011 | Braido |
| 8,052,592 B2 | 11/2011 | Goldfarb |
| 8,057,493 B2 | 11/2011 | Goldfarb |
| 8,070,802 B2 | 12/2011 | Lamphere |
| 8,083,793 B2 | 12/2011 | Lane |
| D653,341 S | 1/2012 | Braido |
| D653,342 S | 1/2012 | Braido |
| 8,092,524 B2 | 1/2012 | Nugent |
| 8,142,492 B2 | 3/2012 | Forster |
| 8,147,541 B2 | 4/2012 | Forster |
| D660,433 S | 5/2012 | Braido |
| D660,967 S | 5/2012 | Braido |
| 8,167,932 B2 | 5/2012 | Bourang |
| 8,236,049 B2 | 8/2012 | Rowe |
| 8,246,677 B2 | 8/2012 | Ryan |
| 8,252,051 B2 | 8/2012 | Chau |
| 8,287,538 B2 | 10/2012 | Brenzel et al. |
| 8,308,798 B2 | 11/2012 | Pintor |
| 8,348,998 B2 | 1/2013 | Pintor |
| 8,348,999 B2 | 1/2013 | Kheradvar |
| 8,366,768 B2 | 2/2013 | Zhang |
| 8,398,708 B2 | 3/2013 | Meiri |
| 8,409,275 B2 | 4/2013 | Matheny |
| 8,414,644 B2 | 4/2013 | Quadri |
| 8,414,645 B2 | 4/2013 | Dwork |
| 8,439,970 B2 | 5/2013 | Jimenez |
| 8,454,686 B2 | 6/2013 | Alkhatib |
| 8,465,541 B2 | 6/2013 | Dwork |
| 8,491,650 B2 | 7/2013 | Wiemeyer |
| 8,512,400 B2 | 8/2013 | Tran |
| 8,518,106 B2 | 8/2013 | Duffy |
| 8,535,373 B2 | 9/2013 | Stacchino |
| 8,562,673 B2 | 10/2013 | Yeung |
| 8,568,472 B2 | 10/2013 | Marchand |
| 8,579,963 B2 | 11/2013 | Tabor |
| 8,579,964 B2 | 11/2013 | Lane |
| 8,603,159 B2 | 12/2013 | Seguin |
| 8,623,075 B2 | 1/2014 | Murray, III |
| 8,636,764 B2 | 1/2014 | Miles |
| 8,641,757 B2 | 2/2014 | Pintor |
| 8,657,870 B2 | 2/2014 | Turovskiy |
| 8,663,318 B2 | 3/2014 | Ho |
| 8,679,176 B2 | 3/2014 | Matheny |
| 8,721,715 B2 | 5/2014 | Wang |
| 8,740,976 B2 | 6/2014 | Tran |
| 8,747,459 B2 | 6/2014 | Nguyen |
| 8,747,461 B2 | 6/2014 | Centola |
| 8,764,793 B2 | 7/2014 | Lee |
| 8,764,820 B2 | 7/2014 | Dehdashtian |
| 8,778,020 B2 | 7/2014 | Gregg |
| 8,790,396 B2 | 7/2014 | Bergheim |
| 8,795,354 B2 | 8/2014 | Benichou |
| 8,795,357 B2 | 8/2014 | Yohanan |
| 8,805,466 B2 | 8/2014 | Salahieh |
| 8,814,931 B2 | 8/2014 | Wang |
| 8,828,043 B2 | 9/2014 | Chambers |
| 8,828,051 B2 | 9/2014 | Javois |
| 8,845,711 B2 | 9/2014 | Miles |
| 8,845,722 B2 | 9/2014 | Gabbay |
| 8,852,271 B2 | 10/2014 | Murray, III |
| 8,852,272 B2 | 10/2014 | Gross |
| 8,870,949 B2 | 10/2014 | Rowe |
| 8,876,897 B2 | 11/2014 | Kheradvar |
| 8,906,022 B2 | 12/2014 | Krinke et al. |
| 8,926,692 B2 | 1/2015 | Dwork |
| 8,956,402 B2 | 2/2015 | Cohn |
| 8,956,405 B2 | 2/2015 | Wang |
| 8,961,518 B2 | 2/2015 | Kyle et al. |
| 8,986,372 B2 | 3/2015 | Murry, III |
| 8,986,374 B2 | 3/2015 | Cao |
| 8,986,375 B2 | 3/2015 | Garde |
| 8,998,980 B2 | 4/2015 | Shipley |
| 8,998,982 B2 | 4/2015 | Richter |
| 9,005,273 B2 | 4/2015 | Salahieh |
| 9,011,527 B2 | 4/2015 | Li |
| D730,520 S | 5/2015 | Braido |
| D730,521 S | 5/2015 | Braido |
| 9,023,101 B2 | 5/2015 | Krahbichler |
| 9,050,188 B2 | 6/2015 | Schweich, Jr. |
| 9,060,855 B2 | 6/2015 | Tuval |
| 9,060,857 B2 | 6/2015 | Nguyen |
| 9,060,858 B2 | 6/2015 | Thornton |
| 9,061,119 B2 | 6/2015 | Le |
| 9,066,800 B2 | 6/2015 | Clague |
| 9,072,603 B2 | 7/2015 | Tuval |
| 9,101,471 B2 | 8/2015 | Kleinschrodt |
| 9,119,717 B2 | 9/2015 | Wang |
| 9,132,008 B2 | 9/2015 | Dwork |
| 9,132,009 B2 | 9/2015 | Hacohen |
| 9,138,313 B2 | 9/2015 | McGuckin, Jr. |
| 9,144,493 B2 | 9/2015 | Carr |
| 9,144,494 B2 | 9/2015 | Murray |

(56) References Cited

U.S. PATENT DOCUMENTS

| | | |
|---|---|---|
| 9,155,619 B2 | 10/2015 | Liu |
| 9,161,835 B2 | 10/2015 | Rankin |
| 9,173,737 B2 | 11/2015 | Hill |
| 9,192,466 B2 | 11/2015 | Kovalsky |
| 9,226,820 B2 | 1/2016 | Braido |
| 9,232,942 B2 | 1/2016 | Seguin |
| 9,232,996 B2 | 1/2016 | Sun |
| 9,248,016 B2 | 2/2016 | Oba |
| 9,259,315 B2 | 2/2016 | Zhou |
| 9,271,856 B2 | 3/2016 | Duffy |
| 9,277,993 B2 | 3/2016 | Gamarra |
| 9,289,289 B2 | 3/2016 | Rolando |
| 9,289,292 B2 | 3/2016 | Anderl |
| 9,295,547 B2 | 3/2016 | Costello |
| 9,295,549 B2 | 3/2016 | Braido |
| 9,301,836 B2 | 4/2016 | Buchbinder |
| 9,301,839 B2 | 4/2016 | Stante |
| 9,320,597 B2 | 4/2016 | Savage |
| 9,320,599 B2 | 4/2016 | Salahieh |
| 9,326,853 B2 | 5/2016 | Olson |
| 9,326,854 B2 | 5/2016 | Casley |
| 9,333,075 B2 | 5/2016 | Biadillah |
| 9,345,572 B2 | 5/2016 | Cerf |
| 9,351,831 B2 | 5/2016 | Braido |
| 9,358,108 B2 | 6/2016 | Bortlein |
| 9,364,325 B2 | 6/2016 | Alon |
| 9,364,637 B2 | 6/2016 | Rothstein |
| 9,370,422 B2 | 6/2016 | Wang |
| 9,387,106 B2 | 7/2016 | Stante |
| 9,402,720 B2 | 8/2016 | Richter |
| 9,414,910 B2 | 8/2016 | Lim |
| 9,414,917 B2 | 8/2016 | Young |
| 9,427,316 B2 | 8/2016 | Schweich, Jr. |
| 9,439,763 B2 | 9/2016 | Geist |
| 9,439,795 B2 | 9/2016 | Wang |
| 9,480,560 B2 | 11/2016 | Quadri |
| 9,498,370 B2 | 11/2016 | Kyle et al. |
| 9,504,569 B2 | 11/2016 | Malewicz |
| 9,522,062 B2 | 12/2016 | Tuval |
| 9,566,152 B2 | 2/2017 | Schweich, Jr. |
| 9,579,194 B2 | 2/2017 | Elizondo |
| 9,579,197 B2 | 2/2017 | Duffy |
| 9,622,863 B2 | 4/2017 | Karapetian |
| 9,717,592 B2 | 8/2017 | Thapliyal |
| 9,730,791 B2 | 8/2017 | Ratz |
| 9,737,400 B2 | 8/2017 | Fish |
| 9,737,401 B2 | 8/2017 | Conklin |
| 9,750,604 B2 | 9/2017 | Naor |
| 9,763,780 B2 | 9/2017 | Morriss |
| 9,795,477 B2 | 10/2017 | Tran |
| 9,801,711 B2 | 10/2017 | Gainor |
| 9,827,093 B2 | 11/2017 | Cartledge |
| 9,839,517 B2 | 12/2017 | Centola et al. |
| 9,839,765 B2 | 12/2017 | Morris |
| 9,861,477 B2 | 1/2018 | Backus |
| 9,872,765 B2 | 1/2018 | Zeng |
| 9,877,830 B2 | 1/2018 | Lim |
| 9,968,443 B2 | 5/2018 | Bruchman |
| 10,004,601 B2 | 6/2018 | Tuval |
| 10,016,274 B2 | 7/2018 | Tabor |
| 10,016,275 B2 | 7/2018 | Nyuli |
| 10,022,132 B2 | 7/2018 | Wlodarski et al. |
| 10,034,750 B2 | 7/2018 | Morriss |
| 10,039,637 B2 | 8/2018 | Maimon |
| 10,039,642 B2 | 8/2018 | Hillukka |
| 10,098,735 B2 | 10/2018 | Lei |
| 10,098,763 B2 | 10/2018 | Lei |
| 10,117,742 B2 | 11/2018 | Braido |
| 10,143,551 B2 | 12/2018 | Braido |
| 10,182,907 B2 | 1/2019 | Lapeyre |
| 10,195,023 B2 | 2/2019 | Wrobel |
| 10,226,340 B2 | 3/2019 | Keren |
| 10,231,834 B2 | 3/2019 | Keidar |
| 10,238,490 B2 | 3/2019 | Gifford, III |
| 10,245,145 B2 | 4/2019 | Mantanus |
| 10,258,464 B2 | 4/2019 | Delaloye |
| 10,299,917 B2 | 5/2019 | Morriss |
| 10,321,990 B2 | 6/2019 | Braido |
| 10,327,892 B2 | 6/2019 | O'Connor |
| 10,327,893 B2 | 6/2019 | Maiorano |
| 10,350,065 B2 | 7/2019 | Quadri |
| 10,357,360 B2 | 7/2019 | Hariton |
| 10,368,982 B2 | 8/2019 | Weber |
| 10,376,363 B2 | 8/2019 | Quadri |
| 10,383,725 B2 | 8/2019 | Chambers |
| 10,390,943 B2 | 8/2019 | Hernandez |
| 10,405,974 B2 | 9/2019 | Hayes |
| 10,433,961 B2 | 10/2019 | McLean |
| 10,470,880 B2 | 11/2019 | Braido |
| 10,492,907 B2 | 12/2019 | Duffy |
| 10,500,041 B2 | 12/2019 | Valdez |
| 10,507,107 B2 | 12/2019 | Nathe |
| 10,512,537 B2 | 12/2019 | Corbett |
| 10,512,538 B2 | 12/2019 | Alkhatib |
| 10,517,726 B2 | 12/2019 | Chau |
| 10,524,902 B2 | 1/2020 | Gründeman |
| 10,524,910 B2 | 1/2020 | Hammer |
| 10,531,951 B2 | 1/2020 | Spargias |
| 10,537,427 B2 | 1/2020 | Zeng |
| 10,555,809 B2 | 2/2020 | Hastings |
| 10,555,812 B2 | 2/2020 | Duffy |
| 10,561,495 B2 | 2/2020 | Chambers |
| 10,595,992 B2 | 3/2020 | Chambers |
| 10,610,362 B2 | 4/2020 | Quadri |
| 10,653,523 B2 | 5/2020 | Chambers |
| 10,667,905 B2 | 6/2020 | Ekvall |
| 10,667,909 B2 | 6/2020 | Richter |
| 10,702,379 B2 | 7/2020 | Garde |
| 10,702,380 B2 | 7/2020 | Morriss |
| 10,709,560 B2 | 7/2020 | Kofidis |
| 10,751,169 B2 | 8/2020 | Chambers |
| 10,751,170 B2 | 8/2020 | Richter |
| 10,751,172 B2 | 8/2020 | Para |
| 10,758,265 B2 | 9/2020 | Siegel |
| 10,758,342 B2 | 9/2020 | Chau |
| 10,779,935 B2 | 9/2020 | Scorsin |
| 10,779,936 B2 | 9/2020 | Pollak |
| 10,779,968 B2 | 9/2020 | Giasolli |
| 10,786,351 B2 | 9/2020 | Christianson |
| 10,828,152 B2 | 11/2020 | Chambers |
| 10,856,983 B2 | 12/2020 | Keränen |
| 10,869,756 B2 | 12/2020 | Al-Jilaihawi |
| 10,874,513 B2 | 12/2020 | Chambers |
| 10,945,835 B2 | 3/2021 | Morriss |
| 10,973,630 B2 | 4/2021 | Torrianni |
| 10,980,636 B2 | 4/2021 | Delaloye |
| 11,000,000 B2 | 5/2021 | Diedering |
| 11,007,053 B2 | 5/2021 | Braido |
| 11,007,054 B2 | 5/2021 | Braido |
| 11,013,599 B2 | 5/2021 | Subramanian |
| 11,026,782 B2 | 6/2021 | Chambers |
| 11,033,275 B2 | 6/2021 | Franano et al. |
| 11,045,202 B2 | 6/2021 | Amplatz |
| 11,065,113 B2 | 7/2021 | Backus |
| 11,065,116 B2 | 7/2021 | Tegels |
| 11,065,138 B2 | 7/2021 | Schreck |
| 11,096,781 B2 | 8/2021 | Gurovich |
| 11,147,666 B2 | 10/2021 | Braido |
| 11,154,239 B2 | 10/2021 | Toth |
| 11,154,396 B2 | 10/2021 | Dibie |
| 11,154,398 B2 | 10/2021 | Straubinger |
| 11,197,754 B2 | 12/2021 | Saffari |
| 11,207,176 B2 | 12/2021 | Delaloye |
| 11,278,399 B2 | 3/2022 | Liu |
| 11,278,406 B2 | 3/2022 | Straubinger |
| 11,351,028 B2 | 6/2022 | Peterson |
| 11,389,293 B2 | 7/2022 | Torrianni |
| 11,395,734 B2 | 7/2022 | Lee |
| 11,413,141 B2 | 8/2022 | Morin |
| 11,419,716 B2 | 8/2022 | Braido |
| 11,452,628 B2 | 9/2022 | Diedering |
| 11,458,013 B2 | 10/2022 | Righini |
| 2001/0005787 A1 | 6/2001 | Oz |
| 2002/0072710 A1 | 6/2002 | Stewart |

(56) References Cited

U.S. PATENT DOCUMENTS

| | | |
|---|---|---|
| 2002/0161377 A1 | 10/2002 | Rabkin |
| 2003/0057156 A1 | 3/2003 | Peterson |
| 2003/0083730 A1 | 5/2003 | Stinson |
| 2003/0199971 A1 | 10/2003 | Tower |
| 2003/0225445 A1 | 12/2003 | Derus |
| 2003/0233141 A1 | 12/2003 | Israel |
| 2004/0073286 A1 | 4/2004 | Armstrong |
| 2004/0088041 A1 | 5/2004 | Stanford |
| 2004/0210307 A1 | 10/2004 | Khairkhahan |
| 2004/0243107 A1 | 12/2004 | Macoviak |
| 2005/0004641 A1 | 1/2005 | Pappu |
| 2005/0075727 A1 | 4/2005 | Wheatley |
| 2005/0096739 A1 | 5/2005 | Cao |
| 2005/0113861 A1 | 5/2005 | Corcoran |
| 2005/0137622 A1* | 6/2005 | Griffin ............ A61B 17/12136 606/198 |
| 2005/0197694 A1 | 9/2005 | Pai |
| 2005/0273160 A1 | 12/2005 | Lashinski |
| 2006/0142847 A1 | 6/2006 | Shaknovich |
| 2006/0184226 A1 | 8/2006 | Austin |
| 2006/0224183 A1 | 10/2006 | Freudenthal |
| 2006/0229708 A1 | 10/2006 | Powell |
| 2006/0259134 A1 | 11/2006 | Schwammenthal et al. |
| 2006/0271173 A1 | 11/2006 | Delgado, III |
| 2006/0276874 A1 | 12/2006 | Wilson |
| 2007/0016288 A1 | 1/2007 | Gurskis |
| 2007/0173930 A1 | 7/2007 | Sogard |
| 2007/0233223 A1 | 10/2007 | Styrc |
| 2007/0238979 A1 | 10/2007 | Huynh |
| 2007/0239254 A1 | 10/2007 | Chia |
| 2007/0239271 A1 | 10/2007 | Nguyen |
| 2007/0270931 A1 | 11/2007 | Leanna |
| 2007/0275027 A1 | 11/2007 | Wen et al. |
| 2007/0293942 A1 | 12/2007 | Mirzaee |
| 2008/0039928 A1 | 2/2008 | Peacock |
| 2008/0082166 A1 | 4/2008 | Styrc |
| 2008/0262592 A1 | 10/2008 | Jordan |
| 2008/0269877 A1 | 10/2008 | Jenson |
| 2008/0275540 A1 | 11/2008 | Wen |
| 2008/0281398 A1 | 11/2008 | Koss |
| 2008/0288042 A1 | 11/2008 | Purdy |
| 2008/0288055 A1 | 11/2008 | Paul, Jr. |
| 2009/0076585 A1 | 3/2009 | Hendriksen |
| 2009/0082840 A1 | 3/2009 | Rusk |
| 2009/0099640 A1 | 4/2009 | Weng |
| 2009/0099647 A1 | 4/2009 | Glimsdale |
| 2009/0125096 A1 | 5/2009 | Chu |
| 2009/0143852 A1 | 6/2009 | Chambers |
| 2009/0171447 A1 | 7/2009 | Von Segesser |
| 2009/0171456 A1 | 7/2009 | Kveen |
| 2009/0198315 A1 | 8/2009 | Boudjemline |
| 2009/0248134 A1 | 10/2009 | Dierking |
| 2009/0248143 A1 | 10/2009 | Laham |
| 2009/0270967 A1 | 10/2009 | Fleming, III |
| 2009/0276039 A1 | 11/2009 | Meretei |
| 2009/0281609 A1 | 11/2009 | Benichou |
| 2010/0021726 A1 | 1/2010 | Jo |
| 2010/0057192 A1 | 3/2010 | Celermajer |
| 2010/0069948 A1 | 3/2010 | Veznedaroglu |
| 2010/0168839 A1 | 7/2010 | Braido |
| 2010/0174355 A1 | 7/2010 | Boyle |
| 2010/0217260 A1 | 8/2010 | Aramayo |
| 2010/0217261 A1 | 8/2010 | Watson |
| 2010/0217262 A1 | 8/2010 | Stevenson |
| 2010/0217263 A1 | 8/2010 | Tukulj-Popovic |
| 2010/0217264 A1 | 8/2010 | Odom |
| 2010/0217265 A1 | 8/2010 | Chen |
| 2010/0217266 A1 | 8/2010 | Helevirta |
| 2010/0217267 A1 | 8/2010 | Bergin |
| 2010/0217268 A1 | 8/2010 | Bloebaum |
| 2010/0217269 A1 | 8/2010 | Landes |
| 2010/0256749 A1 | 10/2010 | Tran |
| 2010/0262157 A1 | 10/2010 | Silver |
| 2010/0262231 A1 | 10/2010 | Tuval et al. |
| 2011/0022151 A1 | 1/2011 | Shin |
| 2011/0046712 A1 | 2/2011 | Melsheimer |
| 2011/0082539 A1 | 4/2011 | Suri |
| 2011/0082540 A1 | 4/2011 | Forster |
| 2011/0208293 A1 | 8/2011 | Tabor |
| 2011/0218585 A1 | 9/2011 | Krinke et al. |
| 2011/0251676 A1 | 10/2011 | Sweeney |
| 2011/0269051 A1 | 11/2011 | Wijenberg |
| 2011/0301702 A1 | 12/2011 | Rust |
| 2011/0319988 A1 | 12/2011 | Schankereli |
| 2011/0319991 A1 | 12/2011 | Hariton |
| 2012/0016468 A1 | 1/2012 | Robin |
| 2012/0035719 A1 | 2/2012 | Forster |
| 2012/0078356 A1 | 3/2012 | Fish |
| 2012/0083875 A1 | 4/2012 | Johnson |
| 2012/0095551 A1 | 4/2012 | Navia |
| 2012/0101567 A1 | 4/2012 | Jansen |
| 2012/0101571 A1 | 4/2012 | Thambar |
| 2012/0109079 A1 | 5/2012 | Asleson |
| 2012/0197193 A1* | 8/2012 | Krolik ............ A61B 5/6853 604/99.04 |
| 2012/0197390 A1 | 8/2012 | Alkhatib |
| 2012/0209375 A1 | 8/2012 | Madrid |
| 2012/0226130 A1 | 9/2012 | De Graff |
| 2012/0303048 A1 | 11/2012 | Manasse |
| 2012/0323313 A1 | 12/2012 | Seguin |
| 2013/0023852 A1 | 1/2013 | Drasler |
| 2013/0060329 A1 | 3/2013 | Agnew |
| 2013/0066419 A1 | 3/2013 | Gregg |
| 2013/0079872 A1 | 3/2013 | Gallagher |
| 2013/0090728 A1 | 4/2013 | Solem |
| 2013/0096671 A1 | 4/2013 | Iobbi |
| 2013/0123911 A1 | 5/2013 | Chalekian |
| 2013/0138138 A1 | 5/2013 | Clark |
| 2013/0150956 A1 | 6/2013 | Yohanan |
| 2013/0184811 A1 | 7/2013 | Rowe |
| 2013/0190861 A1 | 7/2013 | Chau |
| 2013/0204311 A1 | 8/2013 | Kunis |
| 2013/0204360 A1 | 8/2013 | Gainor |
| 2013/0226286 A1 | 8/2013 | Hargreaves |
| 2013/0231736 A1 | 9/2013 | Essinger |
| 2013/0238089 A1 | 9/2013 | Lichtenstein |
| 2013/0274855 A1* | 10/2013 | Stante ............ A61F 2/2436 623/1.11 |
| 2013/0297010 A1 | 11/2013 | Bishop |
| 2013/0297012 A1 | 11/2013 | Willard |
| 2013/0304197 A1 | 11/2013 | Buchbinder |
| 2013/0310917 A1 | 11/2013 | Richter |
| 2013/0310923 A1 | 11/2013 | Kheradvar |
| 2013/0317598 A1 | 11/2013 | Rowe |
| 2013/0331933 A1 | 12/2013 | Alkhatib |
| 2014/0005768 A1 | 1/2014 | Thomas |
| 2014/0005773 A1 | 1/2014 | Wheatley |
| 2014/0005778 A1 | 1/2014 | Buchbinder |
| 2014/0012371 A1 | 1/2014 | Li |
| 2014/0018841 A1 | 1/2014 | Peiffer |
| 2014/0018906 A1 | 1/2014 | Rafiee |
| 2014/0031928 A1 | 1/2014 | Murphy |
| 2014/0031951 A1 | 1/2014 | Costello |
| 2014/0039613 A1 | 2/2014 | Navia |
| 2014/0046433 A1 | 2/2014 | Kovalsky |
| 2014/0046436 A1 | 2/2014 | Kheradvar |
| 2014/0052238 A1 | 2/2014 | Wang |
| 2014/0052241 A1 | 2/2014 | Harks |
| 2014/0057730 A1 | 2/2014 | Steinhauser |
| 2014/0057731 A1 | 2/2014 | Stephens |
| 2014/0057732 A1 | 2/2014 | Gilbert |
| 2014/0057733 A1 | 2/2014 | Yamamoto |
| 2014/0057734 A1 | 2/2014 | Lu |
| 2014/0057735 A1 | 2/2014 | Yu |
| 2014/0057736 A1 | 2/2014 | Burnett |
| 2014/0057737 A1 | 2/2014 | Solheim |
| 2014/0057738 A1 | 2/2014 | Albertsen |
| 2014/0057739 A1 | 2/2014 | Stites |
| 2014/0067050 A1 | 3/2014 | Costello |
| 2014/0074151 A1 | 3/2014 | Tischler |
| 2014/0081308 A1 | 3/2014 | Wondka |
| 2014/0081375 A1 | 3/2014 | Bardill et al. |
| 2014/0088696 A1 | 3/2014 | Figulla |
| 2014/0114340 A1 | 4/2014 | Zhou |

(56) References Cited

U.S. PATENT DOCUMENTS

| | | |
|---|---|---|
| 2014/0128963 A1 | 5/2014 | Quill |
| 2014/0134322 A1 | 5/2014 | Larsen |
| 2014/0135817 A1 | 5/2014 | Tischler |
| 2014/0135907 A1 | 5/2014 | Gallagher |
| 2014/0142612 A1 | 5/2014 | Li |
| 2014/0142680 A1 | 5/2014 | Laske |
| 2014/0142688 A1 | 5/2014 | Duffy |
| 2014/0142691 A1 | 5/2014 | Pouletty |
| 2014/0163668 A1 | 6/2014 | Rafiee |
| 2014/0172076 A1 | 6/2014 | Jonsson |
| 2014/0172083 A1 | 6/2014 | Bruchman |
| 2014/0180397 A1 | 6/2014 | Gerberding |
| 2014/0180401 A1 | 6/2014 | Quill |
| 2014/0188157 A1 | 7/2014 | Clark |
| 2014/0194979 A1 | 7/2014 | Seguin |
| 2014/0222140 A1 | 8/2014 | Schreck |
| 2014/0228944 A1 | 8/2014 | Paniagua |
| 2014/0236288 A1 | 8/2014 | Lambrecht |
| 2014/0243954 A1 | 8/2014 | Shannon |
| 2014/0243967 A1 | 8/2014 | Salahieh |
| 2014/0243969 A1 | 8/2014 | Venkatasubramanian |
| 2014/0249564 A1 | 9/2014 | Daly |
| 2014/0249621 A1 | 9/2014 | Eidenschink |
| 2014/0257467 A1 | 9/2014 | Lane |
| 2014/0276395 A1 | 9/2014 | Wilson |
| 2014/0277074 A1 | 9/2014 | Kaplan |
| 2014/0277119 A1 | 9/2014 | Akpinar |
| 2014/0277388 A1 | 9/2014 | Skemp |
| 2014/0277389 A1 | 9/2014 | Braido |
| 2014/0277408 A1 | 9/2014 | Folan |
| 2014/0277411 A1 | 9/2014 | Börtlein |
| 2014/0277417 A1 | 9/2014 | Schraut |
| 2014/0277422 A1 | 9/2014 | Ratz |
| 2014/0277424 A1 | 9/2014 | Oslund |
| 2014/0277425 A1 | 9/2014 | Dakin |
| 2014/0277426 A1 | 9/2014 | Dakin |
| 2014/0288634 A1 | 9/2014 | Shalev |
| 2014/0288639 A1 | 9/2014 | Gainor |
| 2014/0296909 A1 | 10/2014 | Heipl |
| 2014/0296969 A1 | 10/2014 | Tegels |
| 2014/0296970 A1 | 10/2014 | Ekvall |
| 2014/0296975 A1 | 10/2014 | Tegels |
| 2014/0309727 A1 | 10/2014 | Lamelas |
| 2014/0330366 A1 | 11/2014 | Dehdashtian |
| 2014/0330368 A1 | 11/2014 | Gloss |
| 2014/0330369 A1 | 11/2014 | Matheny |
| 2014/0330370 A1 | 11/2014 | Matheny |
| 2014/0331475 A1 | 11/2014 | Duffy |
| 2014/0343665 A1 | 11/2014 | Straubinger |
| 2014/0343669 A1 | 11/2014 | Lane |
| 2014/0343670 A1 | 11/2014 | Bakis |
| 2014/0358224 A1 | 12/2014 | Tegels |
| 2014/0371844 A1 | 12/2014 | Dale |
| 2014/0379020 A1 | 12/2014 | Campbell |
| 2015/0005857 A1 | 1/2015 | Kern |
| 2015/0018933 A1 | 1/2015 | Yang |
| 2015/0025621 A1 | 1/2015 | Costello |
| 2015/0025625 A1 | 1/2015 | Rylski |
| 2015/0039081 A1 | 2/2015 | Costello |
| 2015/0039083 A1 | 2/2015 | Rafiee |
| 2015/0066138 A1 | 3/2015 | Alexander |
| 2015/0066141 A1 | 3/2015 | Braido |
| 2015/0073548 A1 | 3/2015 | Matheny |
| 2015/0088248 A1 | 3/2015 | Scorsin |
| 2015/0088251 A1 | 3/2015 | May-Newman |
| 2015/0094802 A1 | 4/2015 | Buchbinder |
| 2015/0094804 A1 | 4/2015 | Bonhoeffer |
| 2015/0112428 A1 | 4/2015 | Daly |
| 2015/0112430 A1 | 4/2015 | Creaven |
| 2015/0119974 A1 | 4/2015 | Rothstein |
| 2015/0119978 A1 | 4/2015 | Tegels |
| 2015/0119980 A1 | 4/2015 | Beith |
| 2015/0119982 A1 | 4/2015 | Quill |
| 2015/0127032 A1 | 5/2015 | Lentz |
| 2015/0127093 A1 | 5/2015 | Hosmer |
| 2015/0127097 A1 | 5/2015 | Neumann |
| 2015/0127100 A1 | 5/2015 | Braido |
| 2015/0134054 A1 | 5/2015 | Morrissey |
| 2015/0142103 A1 | 5/2015 | Vidlund |
| 2015/0142104 A1 | 5/2015 | Braido |
| 2015/0148731 A1 | 5/2015 | McNamara |
| 2015/0150678 A1 | 6/2015 | Brecker |
| 2015/0157455 A1 | 6/2015 | Hoang |
| 2015/0157458 A1 | 6/2015 | Thambar |
| 2015/0173770 A1 | 6/2015 | Warner |
| 2015/0173897 A1 | 6/2015 | Raanani |
| 2015/0173898 A1 | 6/2015 | Drasler |
| 2015/0173899 A1 | 6/2015 | Braido |
| 2015/0196300 A1 | 7/2015 | Tischler |
| 2015/0196390 A1 | 7/2015 | Ma |
| 2015/0196393 A1 | 7/2015 | Vidlund |
| 2015/0209140 A1 | 7/2015 | Bell |
| 2015/0209143 A1 | 7/2015 | Duffy |
| 2015/0223729 A1 | 8/2015 | Balachandran |
| 2015/0223820 A1 | 8/2015 | Olson |
| 2015/0223934 A1 | 8/2015 | Vidlund |
| 2015/0230921 A1 | 8/2015 | Chau |
| 2015/0238312 A1 | 8/2015 | Lashinski |
| 2015/0238313 A1 | 8/2015 | Spence |
| 2015/0257879 A1 | 9/2015 | Bortlein |
| 2015/0257880 A1 | 9/2015 | Bortlein |
| 2015/0257881 A1 | 9/2015 | Bortlein |
| 2015/0257882 A1 | 9/2015 | Bortlein |
| 2015/0265402 A1 | 9/2015 | Centola |
| 2015/0265404 A1 | 9/2015 | Rankin |
| 2015/0272730 A1 | 10/2015 | Melnick |
| 2015/0272731 A1 | 10/2015 | Racchini |
| 2015/0272738 A1 | 10/2015 | Sievers |
| 2015/0282931 A1 | 10/2015 | Brunnett |
| 2015/0282958 A1 | 10/2015 | Centola |
| 2015/0289972 A1 | 10/2015 | Yang |
| 2015/0289974 A1 | 10/2015 | Matheny |
| 2015/0289977 A1 | 10/2015 | Kovalsky |
| 2015/0290007 A1 | 10/2015 | Aggerholm |
| 2015/0297346 A1 | 10/2015 | Duffy |
| 2015/0297381 A1 | 10/2015 | Essinger |
| 2015/0305860 A1 | 10/2015 | Wang |
| 2015/0305861 A1 | 10/2015 | Annest |
| 2015/0313710 A1 | 11/2015 | Eberhardt |
| 2015/0313712 A1 | 11/2015 | Carpentier |
| 2015/0320552 A1 | 11/2015 | Letac |
| 2015/0320556 A1 | 11/2015 | Levi |
| 2015/0327995 A1 | 11/2015 | Morin |
| 2015/0327996 A1 | 11/2015 | Fahim |
| 2015/0327999 A1 | 11/2015 | Board |
| 2015/0328000 A1 | 11/2015 | Ratz et al. |
| 2015/0335422 A1 | 11/2015 | Straka |
| 2015/0342718 A1 | 12/2015 | Weber |
| 2015/0342734 A1 | 12/2015 | Braido |
| 2015/0351735 A1 | 12/2015 | Keranen |
| 2015/0351904 A1 | 12/2015 | Cooper |
| 2015/0351905 A1 | 12/2015 | Benson |
| 2015/0359628 A1 | 12/2015 | Keranen |
| 2015/0359629 A1 | 12/2015 | Ganesan |
| 2015/0366665 A1 | 12/2015 | Lombardi |
| 2015/0366667 A1 | 12/2015 | Bailey |
| 2015/0366690 A1 | 12/2015 | Lumauig |
| 2015/0374490 A1 | 12/2015 | Alkhatib |
| 2015/0374906 A1 | 12/2015 | Forsell |
| 2016/0000559 A1 | 1/2016 | Chen |
| 2016/0000562 A1 | 1/2016 | Siegel |
| 2016/0008128 A1 | 1/2016 | Squara |
| 2016/0008131 A1 | 1/2016 | Christianson |
| 2016/0015512 A1 | 1/2016 | Zhang |
| 2016/0015515 A1 | 1/2016 | Lashinski |
| 2016/0022417 A1 | 1/2016 | Karapetian |
| 2016/0022418 A1 | 1/2016 | Salahieh |
| 2016/0030165 A1 | 2/2016 | Mitra |
| 2016/0030168 A1 | 2/2016 | Spenser |
| 2016/0030169 A1 | 2/2016 | Shahriari |
| 2016/0030170 A1 | 2/2016 | Alkhatib |
| 2016/0030171 A1 | 2/2016 | Quijano |
| 2016/0030173 A1 | 2/2016 | Cai |
| 2016/0030175 A1 | 2/2016 | Madjarov |

(56) References Cited

U.S. PATENT DOCUMENTS

| | | |
|---|---|---|
| 2016/0038283 A1 | 2/2016 | Divekar |
| 2016/0045306 A1 | 2/2016 | Agrawal |
| 2016/0045308 A1 | 2/2016 | Macoviak |
| 2016/0045309 A1 | 2/2016 | Valdez |
| 2016/0045310 A1 | 2/2016 | Alkhatib |
| 2016/0045311 A1 | 2/2016 | McCann |
| 2016/0051358 A1 | 2/2016 | Sutton |
| 2016/0051362 A1 | 2/2016 | Cooper |
| 2016/0051364 A1 | 2/2016 | Cunningham |
| 2016/0066922 A1 | 3/2016 | Bridgeman |
| 2016/0067038 A1 | 3/2016 | Park |
| 2016/0067041 A1 | 3/2016 | Alkhatib |
| 2016/0074161 A1 | 3/2016 | Bennett |
| 2016/0074164 A1 | 3/2016 | Naor |
| 2016/0074165 A1 | 3/2016 | Spence |
| 2016/0081799 A1 | 3/2016 | Leo |
| 2016/0089234 A1 | 3/2016 | Gifford, III |
| 2016/0089235 A1 | 3/2016 | Yellin |
| 2016/0089236 A1 | 3/2016 | Kovalsky |
| 2016/0095700 A1 | 4/2016 | Righini |
| 2016/0095701 A1 | 4/2016 | Dale |
| 2016/0095702 A1 | 4/2016 | Gainor |
| 2016/0095703 A1 | 4/2016 | Thomas |
| 2016/0095704 A1 | 4/2016 | Whitman |
| 2016/0100844 A1 | 4/2016 | Li |
| 2016/0100939 A1 | 4/2016 | Armstrong |
| 2016/0100941 A1 | 4/2016 | Czyscon |
| 2016/0100942 A1 | 4/2016 | Morrissey |
| 2016/0106539 A1 | 4/2016 | Buchbinder |
| 2016/0113764 A1 | 4/2016 | Sheahan |
| 2016/0113766 A1 | 4/2016 | Ganesan |
| 2016/0113767 A1 | 4/2016 | Miller |
| 2016/0113768 A1 | 4/2016 | Ganesan |
| 2016/0120642 A1 | 5/2016 | Shaolian |
| 2016/0120643 A1 | 5/2016 | Kupumbati |
| 2016/0120646 A1 | 5/2016 | Dwork |
| 2016/0135951 A1 | 5/2016 | Salahieh |
| 2016/0136412 A1 | 5/2016 | McKinnon |
| 2016/0143730 A1 | 5/2016 | Kheradvar |
| 2016/0143731 A1 | 5/2016 | Backus |
| 2016/0143734 A1 | 5/2016 | Shaolian |
| 2016/0151155 A1 | 6/2016 | Lutter |
| 2016/0157998 A1 | 6/2016 | Bruchman |
| 2016/0157999 A1 | 6/2016 | Lane |
| 2016/0158001 A1 | 6/2016 | Wallace |
| 2016/0158004 A1 | 6/2016 | Kumar |
| 2016/0158007 A1 | 6/2016 | Centola |
| 2016/0158011 A1 | 6/2016 | De Canniere |
| 2016/0158013 A1 | 6/2016 | Carpentier |
| 2016/0166381 A1 | 6/2016 | Sugimoto |
| 2016/0166382 A1 | 6/2016 | Nguyen |
| 2016/0166384 A1 | 6/2016 | Olson |
| 2016/0175096 A1 | 6/2016 | Dienno |
| 2016/0193044 A1 | 7/2016 | Achiluzzi |
| 2016/0193045 A1 | 7/2016 | Pollak |
| 2016/0193047 A1 | 7/2016 | Delaloye |
| 2016/0199177 A1 | 7/2016 | Spence |
| 2016/0199178 A1 | 7/2016 | Venkatasubramanian |
| 2016/0199180 A1 | 7/2016 | Zeng |
| 2016/0199182 A1 | 7/2016 | Gorman, III |
| 2016/0213470 A1 | 7/2016 | Ahlberg |
| 2016/0220363 A1 | 8/2016 | Peter |
| 2016/0235525 A1 | 8/2016 | Rothstein |
| 2016/0235530 A1 | 8/2016 | Thomas |
| 2016/0235531 A1 | 8/2016 | Ciobanu |
| 2016/0250022 A1 | 9/2016 | Braido |
| 2016/0250051 A1 | 9/2016 | Lim |
| 2016/0256168 A1 | 9/2016 | Nielsen |
| 2016/0256270 A1 | 9/2016 | Folan |
| 2016/0262884 A1 | 9/2016 | Lombardi |
| 2016/0270910 A1 | 9/2016 | Birmingham |
| 2016/0270911 A1 | 9/2016 | Ganesan |
| 2016/0278922 A1 | 9/2016 | Braido |
| 2016/0296323 A1 | 10/2016 | Wulfman |
| 2016/0296333 A1 | 10/2016 | Balachandran |
| 2016/0302920 A1 | 10/2016 | Al-Jilaihawi |
| 2016/0302921 A1 | 10/2016 | Gosal |
| 2016/0302922 A1 | 10/2016 | Keidar |
| 2016/0310268 A1 | 10/2016 | Oba |
| 2016/0324640 A1 | 11/2016 | Gifford, III |
| 2016/0331529 A1 | 11/2016 | Marchand |
| 2016/0346081 A1 | 12/2016 | Zeng |
| 2016/0354203 A1 | 12/2016 | Tuval et al. |
| 2016/0361161 A1 | 12/2016 | Braido |
| 2016/0374790 A1 | 12/2016 | Jacinto |
| 2016/0374801 A1 | 12/2016 | Jimenez |
| 2016/0374802 A1 | 12/2016 | Levi |
| 2016/0374803 A1 | 12/2016 | Figulla |
| 2016/0374842 A1 | 12/2016 | Havel |
| 2017/0079781 A1 | 3/2017 | Lim |
| 2017/0079785 A1 | 3/2017 | Li |
| 2017/0079787 A1 | 3/2017 | Benson |
| 2017/0079790 A1 | 3/2017 | Vidlund |
| 2017/0086973 A1 | 3/2017 | Zeng |
| 2017/0095256 A1 | 4/2017 | Lindgren |
| 2017/0100241 A1 | 4/2017 | Modine |
| 2017/0105839 A1 | 4/2017 | Subramanian |
| 2017/0165066 A1 | 6/2017 | Rothstein |
| 2017/0172737 A1 | 6/2017 | Kuetting |
| 2017/0202525 A1 | 7/2017 | Piazza |
| 2017/0231761 A1 | 8/2017 | Cohen-Tzemach et al. |
| 2017/0252191 A1 | 9/2017 | Pacetti |
| 2017/0281193 A1 | 10/2017 | Asirvatham |
| 2017/0348098 A1 | 12/2017 | Rowe |
| 2017/0360570 A1 | 12/2017 | Berndt et al. |
| 2018/0014830 A1 | 1/2018 | Neumann |
| 2018/0049873 A1 | 2/2018 | Manash et al. |
| 2018/0055629 A1 | 3/2018 | Oba et al. |
| 2018/0092744 A1 | 4/2018 | Von Oepen |
| 2018/0110622 A1 | 4/2018 | Gregg et al. |
| 2018/0116843 A1 | 5/2018 | Schreck |
| 2018/0116848 A1 | 5/2018 | McHugo |
| 2018/0133012 A1 | 5/2018 | Nathe |
| 2018/0185184 A1 | 7/2018 | Christakis |
| 2018/0193153 A1 | 7/2018 | Brenzel et al. |
| 2018/0206983 A1 | 7/2018 | Noe |
| 2018/0256329 A1 | 9/2018 | Chambers |
| 2018/0296335 A1 | 10/2018 | Miyashiro |
| 2018/0311039 A1 | 11/2018 | Cohen |
| 2018/0325664 A1 | 11/2018 | Gonda |
| 2018/0333102 A1 | 11/2018 | De Haan et al. |
| 2018/0360602 A1 | 12/2018 | Kumar |
| 2018/0369006 A1 | 12/2018 | Zhang |
| 2019/0053898 A1 | 2/2019 | Maimon et al. |
| 2019/0099265 A1 | 4/2019 | Braido |
| 2019/0105088 A1 | 4/2019 | Peterson et al. |
| 2019/0151067 A1 | 5/2019 | Zucker |
| 2019/0201192 A1 | 7/2019 | Kruse |
| 2019/0224028 A1 | 7/2019 | Finn |
| 2019/0247189 A1 | 8/2019 | Dale |
| 2019/0247190 A1 | 8/2019 | Nathe |
| 2019/0321530 A1 | 10/2019 | Cambronne |
| 2019/0321531 A1 | 10/2019 | Cambronne |
| 2019/0365534 A1 | 12/2019 | Kramer |
| 2019/0365538 A1 | 12/2019 | Chambers |
| 2020/0000592 A1 | 1/2020 | Lee |
| 2020/0030088 A1 | 1/2020 | Vidlund |
| 2020/0030507 A1 | 1/2020 | Higgins |
| 2020/0069423 A1 | 3/2020 | Peterson |
| 2020/0069449 A1 | 3/2020 | Diedering |
| 2020/0100897 A1 | 4/2020 | McLean |
| 2020/0113682 A1 | 4/2020 | Chang |
| 2020/0113719 A1* | 4/2020 | Desrosiers ......... A61B 17/3468 |
| 2020/0129294 A1 | 4/2020 | Hariton |
| 2020/0155306 A1 | 5/2020 | Bonyuet |
| 2020/0163765 A1 | 5/2020 | Christianson |
| 2020/0179111 A1 | 6/2020 | Vidlund |
| 2020/0179115 A1 | 6/2020 | Chambers |
| 2020/0188101 A1 | 6/2020 | Chambers |
| 2020/0222179 A1 | 7/2020 | Chambers |
| 2020/0253733 A1 | 8/2020 | Subramanian |
| 2020/0261219 A1 | 8/2020 | Kumar |
| 2020/0276013 A1 | 9/2020 | Chambers |
| 2020/0315678 A1 | 10/2020 | Mazzio et al. |

(56) References Cited

U.S. PATENT DOCUMENTS

| | | |
|---|---|---|
| 2020/0337765 A1 | 10/2020 | Smith |
| 2020/0368023 A1 | 11/2020 | Kheradvar |
| 2020/0375733 A1 | 12/2020 | Diedering |
| 2021/0236274 A1 | 8/2021 | Benson |
| 2021/0236276 A1 | 8/2021 | Diedering |
| 2021/0275297 A1 | 9/2021 | Berndt |
| 2021/0275301 A1 | 9/2021 | Kumar |
| 2021/0290383 A1 | 9/2021 | Chambers |
| 2022/0031451 A1 | 2/2022 | Spence |
| 2022/0338979 A1 | 10/2022 | Benichou |
| 2023/0218397 A1 | 7/2023 | Chambers et al. |
| 2023/0372089 A1 | 11/2023 | Kumar |
| 2024/0138976 A1 | 5/2024 | Berndt et al. |

FOREIGN PATENT DOCUMENTS

| | | |
|---|---|---|
| AU | 2013201970 B2 | 3/2016 |
| CN | 2820130 Y | 9/2006 |
| CN | 100413471 C | 8/2008 |
| CN | 100444811 C | 12/2008 |
| CN | 101953723 A | 1/2011 |
| CN | 101953724 A | 1/2011 |
| CN | 101953725 A | 1/2011 |
| CN | 101953728 A | 1/2011 |
| CN | 101953729 A | 1/2011 |
| CN | 101961269 A | 2/2011 |
| CN | 101961273 A | 2/2011 |
| CN | 102036622 | 4/2011 |
| CN | 201870772 U | 6/2011 |
| CN | 203290964 U | 11/2013 |
| CN | 103431931 A | 12/2013 |
| CN | 203379235 U | 1/2014 |
| CN | 103598939 A | 2/2014 |
| CN | 103610520 A | 3/2014 |
| CN | 203619728 U | 6/2014 |
| CN | 203677318 U | 7/2014 |
| CN | 104287804 A | 1/2015 |
| CN | 104352261 A | 2/2015 |
| CN | 204133530 U | 2/2015 |
| CN | 204181679 U | 3/2015 |
| CN | 204246182 U | 4/2015 |
| CN | 204318826 U | 5/2015 |
| CN | 104688292 A | 6/2015 |
| CN | 102985033 B | 8/2015 |
| CN | 204581598 U | 8/2015 |
| CN | 204581599 U | 8/2015 |
| CN | 204683686 U | 10/2015 |
| CN | 105596052 A | 5/2016 |
| CN | 105615936 A | 6/2016 |
| CN | 205286438 U | 6/2016 |
| CN | 108348270 | 7/2018 |
| CN | 107252363 B | 4/2020 |
| CN | 106913909 B | 9/2020 |
| CN | 107007887 B | 10/2020 |
| DE | 102010021345 A1 | 11/2011 |
| EP | 2596754 A1 | 5/2013 |
| EP | 2967858 A2 | 1/2016 |
| EP | 2982336 A1 | 2/2016 |
| EP | 2967845 B1 | 8/2018 |
| EP | 2950752 B1 | 7/2022 |
| JP | 2016531722 A | 10/2016 |
| WO | WO1995016476 A1 | 6/1995 |
| WO | WO2009127973 A2 | 10/2009 |
| WO | WO2014210299 A1 | 12/2014 |
| WO | WO2015004173 A1 | 1/2015 |
| WO | WO2016100806 A1 | 6/2016 |
| WO | WO2019006387 | 1/2019 |

OTHER PUBLICATIONS

The AltaValve™. Attributes, Challenges, and Future Programs, Dr. Philippe Genereux, MD, Jun. 22, 2018.

4C Medical's AltaValve: The First-in-Human Experience, Joep Rodes-Cabau, MD, Sep. 21, 2018.

Ferreira-Neto et al., "Transcatheter Mitral Valve Replacement With a New Supra-Annular Valve-First-in-Human Experience with the AltaValve System," https://doi.org/10.1016/j.jcin.2018.10.056, by the American College of Cardiology Foundation Published by Elsevier, Jan. 28, 2019.

Goel et al., "Transcatheter Mitral Valve Therapy with Novel Supra-Annular AltaValve," https://doi.org/10.1016/j.jaccas.2019.10.034, Published by Elsevier on behalf of the American College of Cardiology Foundation, Dec. 18, 2019.

Hatamifar et al., "MRI Evaluation of an Atrial-Anchored Transcatheter Mitral Valve Replacement Implant," https://www.ajronline.org/doi/10.2214/AJR.19.22206 American Roentgen Ray Society, Jan. 15, 2020.

Alperi et al., "Device profile of the AltaValve System for Transcatheter Mitral Valve Replacement: Overview of its safety and Efficacy," https://doi.org/10.1080/17434440.2020.1781616, Informa UK Limited, Jun. 25, 2020.

Extended European Search Report in Application No. 21748274.4, Jan. 22, 2024.

Taiwanese Office Action received in Application No. 110103581, Aug. 7, 2024.

\* cited by examiner

PROSTHETIC HEART VALVE DELIVERY SYSTEM: PADDLE ATTACHMENT FEATURE

CROSS-REFERENCE TO RELATED APPLICATIONS

This application claims the benefit of U.S. Provisional Application No. 62/968,220, filed Jan. 31, 2020, and entitled PROSTHETIC HEART VALVE DELIVERY SYSTEM: PADDLE ATTACHMENT FEATURE

STATEMENT REGARDING FEDERALLY SPONSORED RESEARCH OR DEVELOPMENT

Not Applicable

BACKGROUND OF THE INVENTION

Field of the Invention

The invention relates to devices and methods for implanting devices within a heart chamber.

Description of the Related Art

The human heart comprises four chambers and four heart valves that assist in the forward (antegrade) flow of blood through the heart. The chambers include the left atrium, left ventricle, right atrium and right ventricle. The four heart valves include the mitral valve, the tricuspid valve, the aortic valve and the pulmonary valve. See generally FIG. 1.

The mitral valve is located between the left atrium and left ventricle and helps control the flow of blood from the left atrium to the left ventricle by acting as a one-way valve to prevent backflow into the left atrium. Similarly, the tricuspid valve is located between the right atrium and the right ventricle, while the aortic valve and the pulmonary valve are semilunar valves located in arteries flowing blood away from the heart. The valves are all one-way valves, with leaflets that open to allow forward (antegrade) blood flow, and are critical in assuring the forward-only flow of an adequate supply of blood through the cardiovascular system. The normally functioning valve leaflets close under the pressure exerted by reverse blood to prevent backflow (retrograde) of the blood into the chamber it just flowed out of. For example, the mitral valve when working properly provides a one-way valving between the left atrium and the left ventricle, opening to allow antegrade flow from the left atrium to the left ventricle and closing to prevent retrograde flow from the left ventricle into the left atrium. This retrograde flow, when present, is known as mitral regurgitation or mitral valve regurgitation.

Native heart valves may be, or become, dysfunctional for a variety of reasons and/or conditions including but not limited to trauma, congenital malformations, inflammatory conditions, infectious conditions, other diseases and conditions, and aging. These types of conditions may cause the valve structure to fail to close properly resulting in regurgitant retrograde flow of blood from the left ventricle to the left atrium in the case of a mitral valve failure.

Mitral valve regurgitation is a specific problem resulting from a dysfunctional mitral valve that allows at least some retrograde blood flow back into the left atrium from the right atrium. In some cases, the dysfunction results from mitral valve leaflet(s) that prolapse up into the left atrial chamber, i.e., above the upper surface of the annulus instead of connecting or coapting to block retrograde flow. This backflow of blood places a burden on the left ventricle with a volume load that may lead to a series of left ventricular compensatory adaptations and adjustments, including remodeling of the ventricular chamber size and shape, that vary considerably during the prolonged clinical course of mitral regurgitation.

Regurgitation can be a problem with native heart valves generally, including tricuspid, aortic and pulmonary valves as well as mitral valves.

Native heart valves generally, e.g., mitral valves, therefore, may require functional repair and/or assistance, including a partial or complete replacement. Such intervention may take several forms including open heart surgery and open heart implantation of a replacement heart valve. See e.g., U.S. Pat. No. 4,106,129 (Carpentier), for a procedure that is highly invasive, fraught with patient risks, and requiring not only an extended hospitalization but also a highly painful recovery period.

Less invasive methods and devices for replacing a dysfunctional heart valve are also known and involve percutaneous access and catheter-facilitated delivery of the replacement valve. Stents in general, and prosthetic cardiac valve and left atrial appendage occluding devices specifically, are well known in the art. Most of these solutions involve a replacement heart valve attached to a structural support such as a stent, commonly known in the art, or other form of wire network designed to expand upon release from a delivery catheter. See, e.g., U.S. Pat. No. 3,657,744 (Ersek); U.S. Pat. No. 5,411,552 (Andersen). The self-expansion variants of the supporting stent assist in positioning the valve, and holding the expanded device in position, within the subject heart chamber or vessel. This self-expanded form also presents problems when, as is often the case, the device is not properly positioned in the first positioning attempt and, therefore, must be recaptured and positionally adjusted. This recapturing process in the case of a fully, or even partially, expanded device requires re-collapsing the device to a point that allows the operator to retract the collapsed device back into a delivery sheath or catheter, adjust the inbound position for the device and then re-expand to the proper position by redeploying the positionally-adjusted device distally out of the delivery sheath or catheter. Collapsing the already expanded device is difficult because the expanded stent or wire network is generally designed to achieve the expanded state which also resists contractive or collapsing forces.

Besides the open heart surgical approach discussed above, gaining access to the valve of interest is achieved percutaneously via one of at least the following known access routes: transapical; transfemoral; transatrial; and transseptal; collectively, transcatheter access routes.

Generally, the art is focused on systems and methods that, using one of the above-described known access routes, allow a partial delivery of the collapsed valve device, wherein one end of the device is released from a delivery sheath or catheter and expanded for an initial positioning followed by full release and expansion when proper positioning is achieved. See. e.g., U.S. Pat. No. 8,852,271 (Murray, III); U.S. Pat. No. 8,747,459 (Nguyen); U.S. Pat. No. 8,814,931 (Wang); U.S. Pat. No. 9,402,720 (Richter); U.S. Pat. No. 8,986,372 (Murray. III); and U.S. Pat. No. 9,277,991 (Salahieh); and U.S. Pat. Pub. Nos. 2015/0272731 (Racchini); and 2016/0235531 (Ciobanu). In such transcatheter techniques, the prosthetic valve is generally mounted within a stented frame that is capable of achieving collapsed and expanded states. The device is collapsed and advanced through a sheath or delivery catheter positioned in a blood vessel of the patient until reaching the implantation site. The stented frame is generally released from the catheter or sheath and, by a variety of means, expanded with the valve to the expanded functional size and orientation within the heart. One of the key issues is ease of delivery of the prosthetic valve, including the stent frame and valve in all access routes, including but not limited to transapical delivery. More specifically, it would be advantageous to have an improved delivery system for attaching, loading, translating, delivering, repositioning and resheathing and deploying an expandable stent to, and within, the subject heart chamber. The present invention addresses these, inter alia, issues.

In addition, known "replacement" prosthetic heart valves are intended for full replacement of the native heart valve. Therefore, these replacement heart valves physically engage tissue within the annular throat, i.e., below the annular plane and upper annular surface, and/or valve leaflets, thereby eliminating all remaining functionality of the native valve and making the patient completely reliant on the replacement valve. Generally speaking, it is a preferred solution that maintains and/or retains the native function of a heart valve, thus supplementation of the valve is preferred rather than full replacement. Obviously, there will be cases when native valve has either lost virtually complete functionality before the interventional implantation procedure, or the native valve continues to lose functionality after the implantation procedure. The preferred solution is delivery and implantation of a valve device that will function both as an adjunctive and/or supplementary functional valve as well as be fully capable of replacing the native function of a valve that has lost, or will lose, most or all of its functionality. However, the inventive solutions described infra will apply generally to all types and forms of heart valve devices, unless otherwise specified. The present disclosure also applies, as the skilled artisan will recognize, to stents generally.

Further, known solutions for, e.g., the mitral valve replacement systems, devices and methods require 2-chamber solutions, i.e., there is involvement and engagement of the implanted replacement valve device in the left atrium and the left ventricle. Generally, these solutions include a radially expanding stent in the left atrium, with anchoring or tethering (disposed downward through the native annulus or annular throat) connected from the stent device down through the annular throat, with the sub-annular surface within the left ventricle, the left ventricular chordae tendineae and even into the left ventricle wall surface(s). See, e.g., the MitraClip® marketed by the Abbott Group and currently the only US approved repair device. With the MitraClip® a catheter containing the MitraClip® is inserted into the femoral vein. The device enters the heart through the inferior vena cava to the right atrium and delivered transseptally. The MitraClip® passes through the annulus into the left ventricle and sits below the leaflets, clipping the leaflets to decrease regurgitation.

Such 2-chamber and native annulus solutions are unnecessary bulky and therefore more difficult to deliver and to position/recapture/reposition from a strictly structural perspective. Further, the 2-chamber solutions present difficulties in terms of making the ventricular anchoring and/or tethering connections required to hold position. Moreover, these solutions interfere with the native valve functionality as described above because the device portions that are disposed within the left ventricle must be routed through the native annulus and/or annular throat and native mitral valve, thereby disrupting any remaining coaptation capability of the native leaflets. In addition, the 2-chamber solutions generally require an invasive anchoring of some of the native tissue, resulting in unnecessary trauma and potential complication.

It will be further recognized that the 2-chamber mitral valve solutions require sub-annular and/or ventricular engagement with anchors, tethers and the like precisely because the atrial portion of the device fails to adequately anchor itself to the atrial chamber and/or upper portion of the annulus. Again, some of the embodiments, or portions thereof, described herein are readily applicable to single or 2-chamber solutions, unless otherwise indicated.

Finally, known prosthetic cardiac valves consist of two or three leaflets that are arranged to act as a one-way valve, permitting fluid flow therethrough in the antegrade direction while preventing retrograde flow. The native mitral valve is located retrosternally at the fourth costal cartilage, consisting of an anterior and posterior leaflet, chordae tendineae, papillary muscles, ventricular wall and annulus connected to the atria. Each native leaflet is supported by chordae tendineae that are attached to papillary muscles which become taut with each ventricular contraction preserving valvular competence. Both the anterior and posterior leaflets of the native valve are attached via primary, secondary and tertiary chordae to both the antero-lateral and posterio-medial papillary muscles. A disruption in either papillary muscle in the setting of myocardial injury, can result in dysfunction of either the anterior or posterior leaflet of the mitral valve. Other mechanisms may result in failure of one, or both of the native mitral leaflets. In the case of a single mitral valve leaflet failure, the regurgitation may take the form of a non-central, eccentric jet of blood back into the left atrium. Other leaflet failures may comprise a more centralized regurgitation jet. Known prosthetic valve replacements generally comprise leaflets which are arranged to mimic the native valve structure, which may over time become susceptible to similar regurgitation outcomes.

The applications for collapsible and expandable stents are not limited to prosthetic heart valve implants. Vascular stents are commonly used and are generally collapsible to facilitate delivery through the lumen of a delivery catheter to the working site where the stent is translated out of the lumen of the catheter and it is expanded, either by a self-expanding means or through an expanding mechanism such as, inter alia, an expandable balloon.

As discussed above, known delivery methods and devices comprise expandable prosthetic valve stents and vascular stents that are collapsed during delivery via a delivery catheter. Some issues with known systems, devices and methods include ease of attaching to, and releasing from, an expandable stent for: loading and/or collapsing the expandable stent into a delivery catheter or sheath, translating the collapsed stent along the delivery catheter or sheath, delivering the expandable stent into the subject heart chamber, repositioning the expandable stent as necessary within the subject heart chamber, recapturing or resheathing the expandable stent within the delivery catheter or sheath if needed, and deploying the expandable stent to, and within, the subject heart chamber. The present invention also addresses these, inter alia, issues.

BRIEF SUMMARY OF THE INVENTION

The present invention provides systems, devices and methods for attaching to, and releasing from, at least one tether connected to and extending from an expandable stent for: loading and/or collapsing the expandable stent into a delivery catheter or sheath, translating the collapsed stent along the delivery catheter or sheath, delivering the expandable stent into the subject heart chamber, repositioning the expandable stent as necessary within the subject heart chamber, recapturing or resheathing the expandable stent within the delivery catheter or sheath if needed, and deploying the expandable stent to, and within, the subject heart chamber. The delivery system embodiments described herein apply to stents comprising single-chamber prosthetic heart valves as well as stents comprising prosthetic heart valves that require anchoring outside of a single chamber.

In one embodiment, a delivery system for delivering an expandable prosthetic heart valve comprising a self-expanding stent frame comprises: an operating handle comprising at least one push/pull and release mechanism; at least one tether assembly, wherein each of the at least one tether assembly is operatively connected at its distal end to a corresponding one of the at least one push/pull and release mechanism of the operating handle, wherein each of the at least one tether assembly comprises: an outer tube defining a lumen therethrough; a notched wire configured to be slidingly received within the lumen of the outer tube and defining a T-shaped notch at a distal end of the notched wire, wherein the T-shaped notch is configured to be distally extended from the lumen of the outer tube, wherein the T-shaped notch is configured to releasably engage a corresponding attachment feature extending from a downstream end of the self-expanding stent frame.

In another embodiment, a method for delivering and deploying a prosthetic heart valve to a patient's heart chamber comprises: providing the aforementioned delivery system for delivering the expandable prosthetic heart valve comprising a self-expanding stent frame; loading and/or collapsing the expandable prosthetic heart valve into a lumen defined by a delivery catheter or sheath; translating the collapsed prosthetic heart valve through the lumen of the delivery catheter or sheath; delivering the expandable prosthetic heart valve into the patient's heart chamber; repositioning the expandable prosthetic heart valve as necessary within the patient's heart chamber; deploying the expandable prosthetic heart valve to, and within, the patient's heart chamber; and withdrawing the delivery system from the patient.

Certain inventive embodiments described herein are readily applicable to single or two chamber solutions, unless otherwise indicated. Moreover, certain embodiments discussed herein may be applied to preservation and/or replacement of native valve functionality generally, and are not, therefore, limited to prosthetic mitral valve devices but may be extended to include prosthetic tricuspid valve devices, prosthetic aortic devices, prosthetic pulmonary valves, and methods for the loading, delivery, deployment, and positioning of any such valves.

DETAILED DESCRIPTION OF THE INVENTION

Generally, various embodiments of the present invention ae directed to devices and methods for attaching an operator-manipulatable tether(s) to the stent for: loading and/or collapsing the expandable stent into a delivery catheter or sheath, translating the collapsed stent along the delivery catheter or sheath, delivering the expandable stent into the subject heart chamber, repositioning the expandable stent as necessary within the subject heart chamber, recapturing or resheathing the expandable stent within the delivery catheter or sheath if needed, and deploying the expandable stent to, and within, the subject heart chamber.

The support structure or stent has multiple functions to aid with the treatment of cardiac valve regurgitation (mitral or tricuspid). These functions include its function as a scaffold for the functioning prosthetic valve, apposition to the atrial anatomy, optimized radial force for compliance with atrial distension, ability to load and deploy from a minimally invasive delivery system, and geometry to support with mitigating against paravalvular leak (PVL). The design features of the stent are adapted to meet one or more of the functions identified above. Specific design features and attributes for exemplary stents are discussed in detail below to assist in understanding of the utility of the funneling loading device and related methods. As the skilled artisan will recognize, the invention is not limited to prosthetic heart valves comprising stent support structures, but may also be applied to collapsible and expandable stents such as commonly used for intravascular procedures. In addition, the skilled artisan will recognize the utility of the disclosed inventions for use in implanting certain exemplary embodiment stent design concepts that are intended to support minimally invasive procedures for the treatment of valvular regurgitation or other dysfunction in at least mitral, tricuspid, and aortic valves.

The expandable stents of the present invention may be self-expandable (e.g. Nitinol or similar materials) or balloon expandable (e.g. cobalt chromium or similar materials). The stents are typically made of cells that may be open celled diamond like structures or continuous structures that have a working cell element. The stents may also be constructed using tubing, wires, braids or similar structures. Exemplary stent transition sections are described below.

Figure 1:
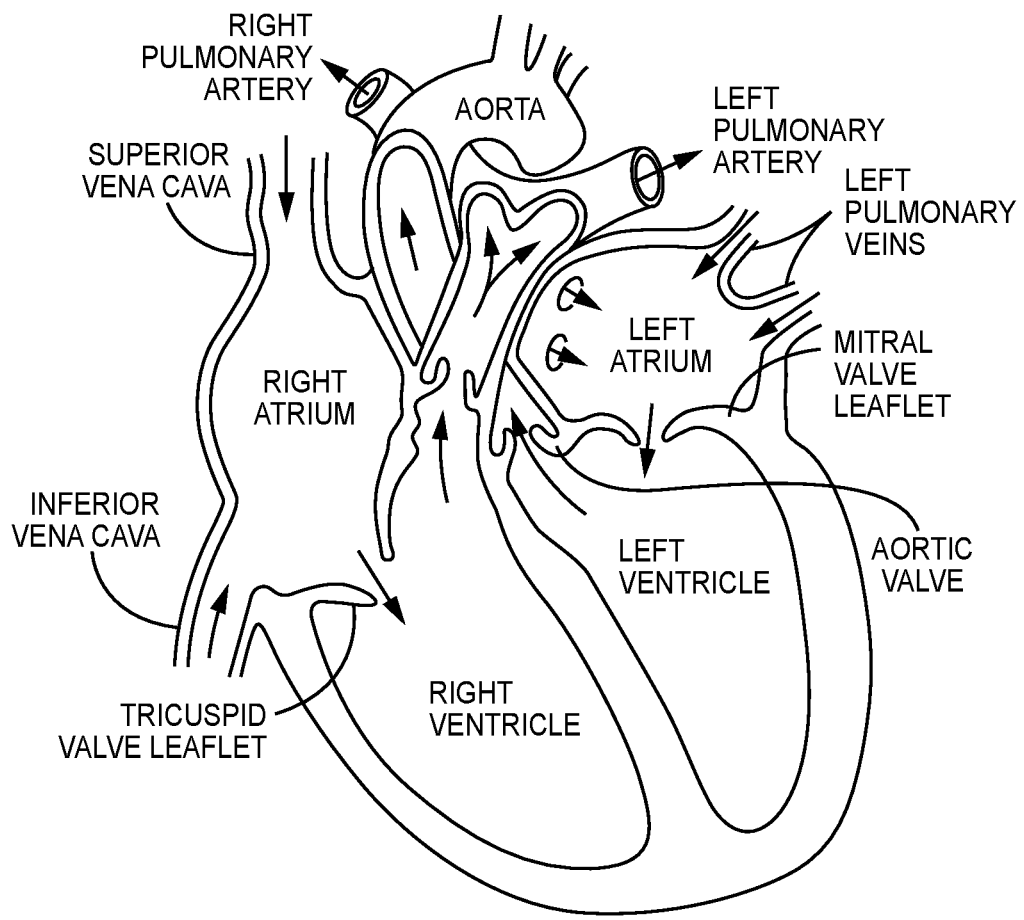
FIG. 1 illustrates certain features of the heart in cross-section.
Figure 2:
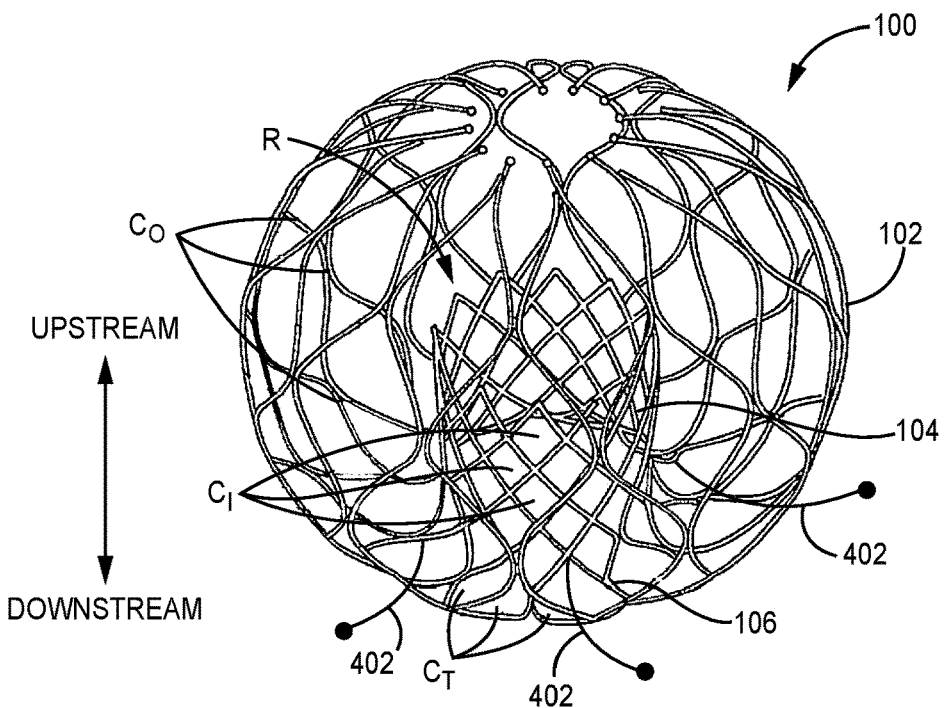
FIG. 2 illustrates a perspective view of an exemplary stent.
Figure 3A:
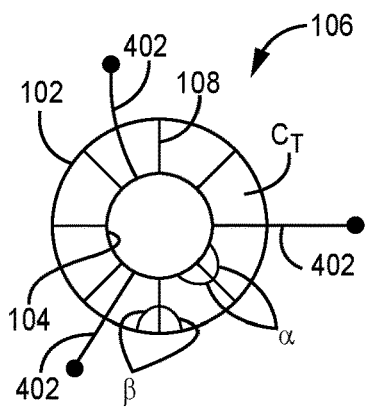
FIG. 3A illustrates a bottom view of one embodiment of the exemplary stent of FIG. 2.
Figure 3B:
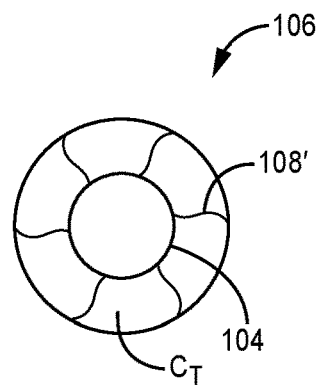
FIG. 3B illustrates a bottom view of one embodiment of a transition section of the exemplary stent of FIG. 2.
Figure 3C:
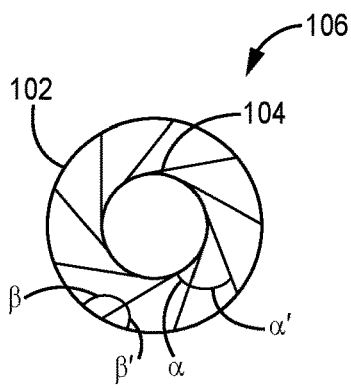
FIG. 3C illustrates a bottom view of one embodiment of a transition section of the exemplary stent of FIG. 2.

With reference now to FIGS. 2-3C, one embodiment of an exemplary expandable stent 100 for use with the present invention comprises a frame defining an outer section 102 and an inner valve support section 104. FIG. 2 illustrates a perspective view of the stent 100. The outer section 102 may generally be circular but need not be a perfectly round circular structure when fully and/or partially expanded. The inner valve support section 104 may be cylindrical—but need not be a constant-diameter cylinder—and is adapted to support and retain prosthetic valve leaflets (not shown in FIG. 2) within the inner valve support section 104. Most preferably, prosthetic valve leaflets are supported and retained within the inner valve support section 104 at a point that is located above the native annulus; e.g., the mitral valve annulus, though other attachment points for the prosthetic leaflets are within the scope of the present invention. Further, as discussed above, the stent 100 may be configured to supplement and/or replace the function of the tricuspid valve. A preferred construction comprises the prosthetic leaflets disposed above the native leaflets, wherein the prosthetic leaflets are attached and spaced sufficiently away from (i.e., above) the native leaflets so as to not physically interfere or interact with the native leaflets. However, certain embodiments contemplate some interaction with the native leaflets.

Individual cells $C_O$ forming the outer section 102 of stent 100 are visible in FIG. 2 as open cell regions defined by the material used to form the exemplary expandable stent 100.

Individual cells $C_I$ forming the inner valve support section 104 are also illustrated as open cells regions formed within an inner region R defined by outer section 102, wherein the inner valve support section extends radially upward into the inner region R. As shown, individual cells $C_I$ are of a different size, and may comprise a different shape, than that of individual cells $C_O$.

The region of the frame of stent 100 that facilitates the radially inward transition of the stent 100 from the outer section 102 to the inner valve support section 104 of the stent 100 is a transition section or cell region 106. Transition cell region 106 may comprise cells $C_T$ that may comprise a different size and/or shape that either the outer section cells $C_O$ and/or the inner section cells $C_I$. The outer section 102, inner valve support section 104, and/or transition cell region 106 of the stent 100 may be constructed from one continuous structure or may combine two or more structures to achieve intended design goals. Transition cell region 106 generally curves radially inward and upward to allow the inner valve support section 104 to reside within the inner region R as shown in FIG. 2. In some embodiments, the lower portion of inner valve support section 104; i.e., the portion of the inner valve support section 104 that is in connection with the cells $C_T$ of transition cell region 106, may also comprise a curving shape to facilitate and/or complete the upward turn into the inner region 102.

FIGS. 3A-3C illustrate bottom views of three different embodiments of the exemplary stent of FIG. 2. Exemplary cross-sectional geometry of the transition cell region 106 viewed from the bottom of stent 100 is represented schematically in FIGS. 3A-3C. This transition cell region 106 of the stent 100 may be a strut, completed cell section or a partial cell section. The transition cell region 106 may have any number of struts (minimum of 3) or cell sections as generally required to meet design needs.

The geometry and/or shape of the transition cells $C_T$ may be substantially straight segments when expanded, as shown in FIG. 3A. For example, transition cells $C_T$ or struts may be evenly spaced and formed by substantially straight and equally spaced apart struts 108 that extend away from the inner valve support section 104 with equal angles α on both sides of the strut 108 and equal angles β on both sides of strut 108 with respect to its intersection or integration with outer support section 102.

In the embodiment of FIG. 3B, the geometry and/or shape of the transition cells $C_T$ may incorporate an offset or a twist in the stent cell pattern. As shown in FIG. 3B, the transition cell region 106 may comprise transition cell struts 108' that comprise transition cells $C_T$ that are formed by struts 108' having an offset, i.e., not straight, are twisted and/or curvilinear. The degree of offset and/or twist and/or curvature of the struts 108', and therefore the size and/or shape of the resultant expanded cells $C_T$, may be varied dependent on the number of cells/struts in the transition cell region 106, packing density when the stent is collapsed, and stress/strain distribution limitations of the transition cell region 106. In this manner the offset or twist in the geometry and/or shape of the transition cells $C_T$ in the embodiment of FIG. 3B may allow for a controlled compression of the stent.

In the embodiment of FIG. 3C, the geometry and/or shape of the transition cells $C_T$ may be substantially straight segments as in FIG. 3A, but with non-equal angles relative to the inner valve support section 104 and outer support section 102. As shown in FIG. 3C, the straight struts 108 of this embodiment are slanted so that a smaller angle α and a larger angle α' are provided relative to the inner valve support section 104. Similarly, a smaller angle β' and a larger angle β are provided relative to the outer support section 102. This allows a compressed nesting of the slanted struts 108 of transition cell region 106.

Attachment features 402 are illustrated in FIGS. 2 and 3A and will be described further below.

Figure 4:
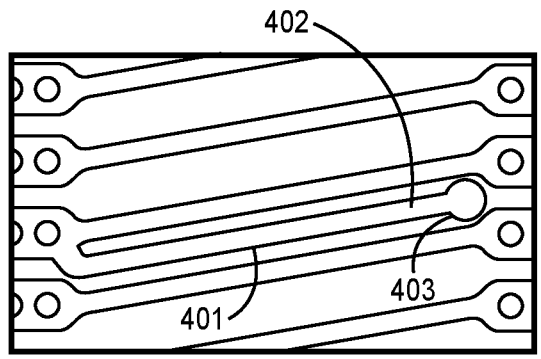
FIG. 4 illustrates one embodiment of an attachment feature defined in an exemplary stent.

FIG. 4 illustrates one embodiment of an attachment feature 402 defined in an exemplary stent such as the stent 100 of FIG. 2. As shown in FIG. 4, an attachment feature 402 is defined within the stent pattern of the frame of stent 100, preferably within the transition cell region 106 of the stent 100. However, the skilled artisan will recognize that attachment feature 402 may also be defined along strut(s) that are not within the transition cell region 106. In addition, attachment feature 402 may be defined at a point on the frame of stent 100 that is on a downstream (of the normal blood flow within the prosthetic heart valve) side of the stent 100 when implanted. Alternatively, attachment feature 402 may be defined on the lowermost downstream strut of the frame of stent 100. Further, attachment features 402 comprise, as best shown in FIG. 4, a wire portion 401 and an enlarged end portion 403 comprising a diameter that is larger than a diameter of the wire portion 401. Enlarged end portion 403 may be circular as shown, or may comprise any number of shapes as will be discussed further below.

Figure 5:
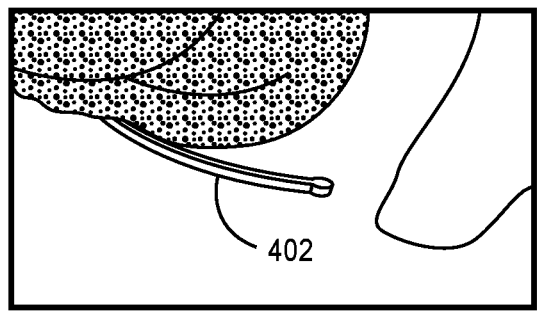
FIG. 5 illustrates one embodiment of an attachment feature extending from a lower section, and extending through a paravalvular leakage mitigating fabric cuff, of the exemplary stent of FIG. 2.

FIG. 5 illustrates one embodiment in which an attachment feature 402 extends from a lower section of the frame of stent 100 of FIG. 2. Attachment feature 402 is, as shown in FIG. 5, adapted to extend outwardly away from the outer section 102 and transition cell region 106. In some cases a paravalvular leakage mitigating fabric skirt or cuff is attached to the outer frame of the stent 100 and at least partially covers the outer section 102 and/or transition cell region 106. In such cases, the attachment feature 402 may pass through the paravalvular leakage mitigating skirt or cuff to outside of the frame of stent 100.

Figure 6:
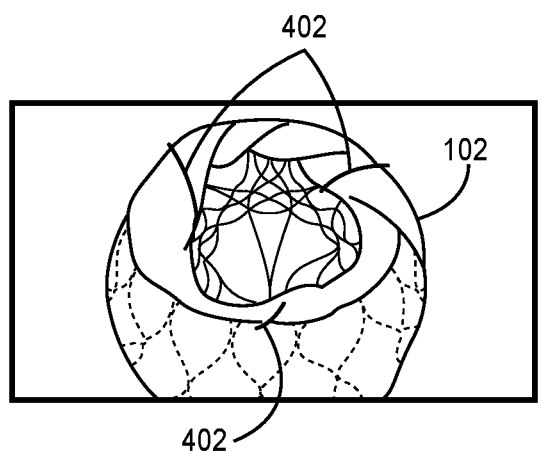
FIG. 6 illustrates one embodiment comprising three attachment features extending from a lower section of the exemplary stent of FIG. 2.
Figure 7:
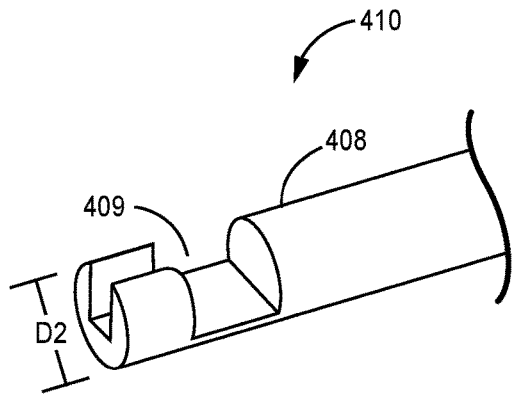
FIG. 7 illustrates one embodiment of a notched wire of a tether attachment and release assembly.
Figure 8:
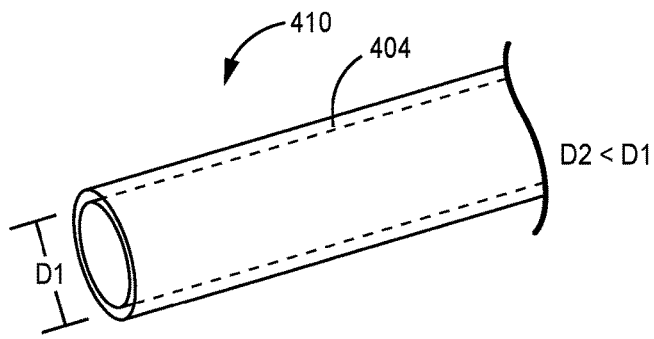
FIG. 8 illustrates one embodiment of an outer tube of a tether assembly.
Figure 9A:
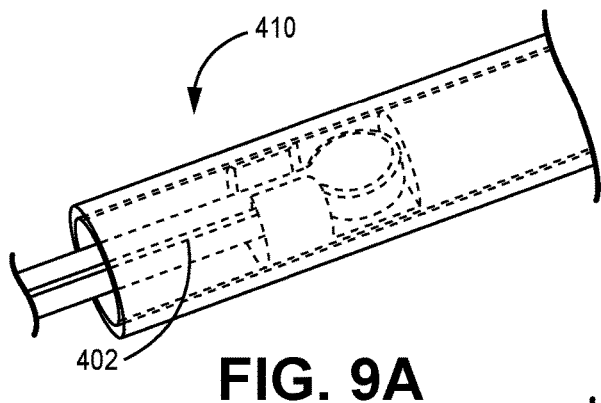
FIG. 9A illustrates one embodiment of a tether assembly in attached engagement with the attachment feature.

In some embodiments an exemplary stent may comprise one or more of the attachment feature 402. FIG. 6 illustrates the locations around a lower portion of the stent 100 for three (3) of the attachment features 402. As shown, there is a substantially equal spacing or separation between adjacent attachment features 402 along and/or around the transition cell region 106. The skilled artisan will recognize the non-equal spacings or separations between the locations of the attachment features 402 may also be employed. In addition, at least one attachment feature 402 may be used. It is preferable to have at least two, and more preferable to have at least three, attachment features 402 defined as described herein. Further, attachment features 402 comprise, as best shown in FIGS. 4 and 9A-9B, a wire portion 401 and an enlarged end portion 403 comprising a diameter that is larger than a diameter of the wire portion 401.

Turning now to FIGS. 7-9C, one embodiment of a tether assembly 410 that is operationally connected at a proximal end to an operational handle, as will be discussed further, is illustrated. Tether assembly 410 further comprises an outer tube 404, and a notched wire 408. The notched wire 408 defines a distal T-shaped engagement channel 409 adapted to provide a complementary fit for the enlarged distal end portion 403 of attachment feature 402 and a section of the wire portion 401 of attachment feature 402. The inner diameter D1 of the lumen of outer tube 404 is larger than outer diameter D2 of notched wire 408. This relationship between D1 and D2 is maintained when the attachment feature 402 is engaged in T-shaped engagement channel 409. This is because, as shown in FIG. 9A, when attachment feature 402 is engaged in engagement channel 409, the outer tube 404 is advanced to cover the engagement channel 409, holding the attachment feature 402 within engagement channel 409. Outer tube 404 defines a lumen therethrough that is sized to allow sliding reception of notched wire 408 within the lumen of outer tube 404.

Figure 9B:
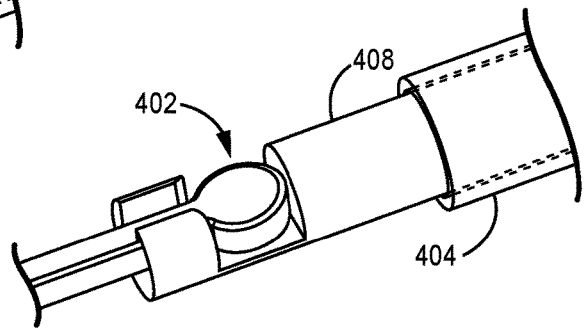
FIG. 9B illustrates the embodiment of FIG. 9A wherein the outer tube of the tether assembly is pulled proximally to expose the attachment feature.
Figure 9C:
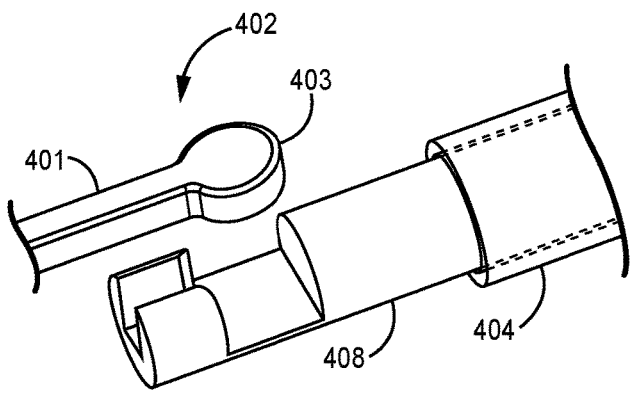
FIG. 9C illustrates the embodiment of FIGS. 9A and 9B wherein the attachment feature is detached and released from the tether assembly.

The outer tube 404 may be proximally withdrawn to expose the attachment feature 402 while attachment feature 402 is engaged in the engagement channel 409, as shown in FIG. 9B, to enable detachment or release of the attachment feature 402 from the notched wire 408. Detachment or release of the attachment feature 402 from the notched wire 408 is illustrated in FIG. 9C.

Figure 11:
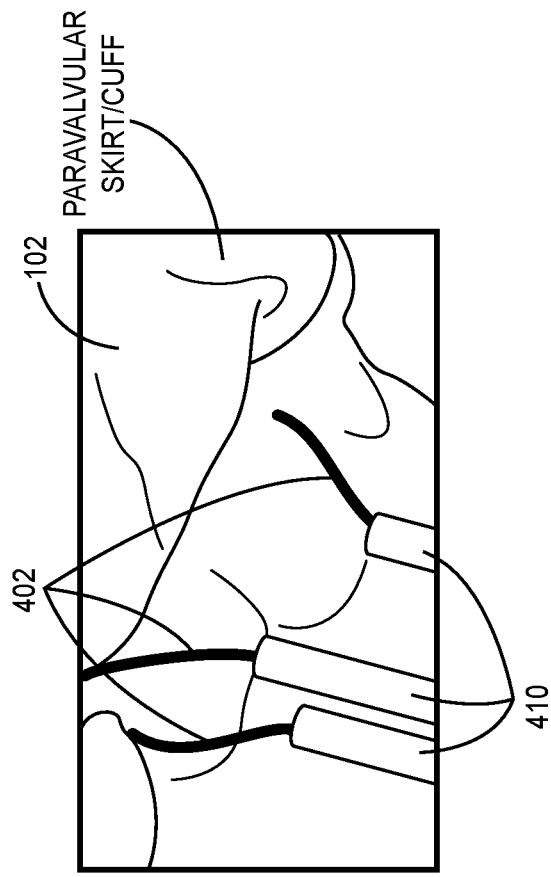
FIG. 11 illustrates each of the three tether assemblies of FIG. 10 in attachment with one of the attachment features.
Figure 10:
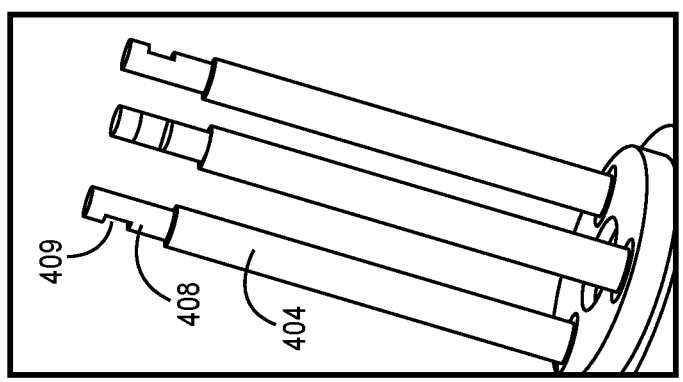
FIG. 10 illustrates one embodiment comprising three (3) tether assemblies extending distally from a delivery catheter or sheath.

FIGS. 10 and 11 provide additional detail for a preferred embodiment comprising three (3) tether assemblies (410). Each of the tether assembly(ies) 410 defines a length that enables proximal connection of the tether assembly 410 with an operating handle (further described below with respect to FIGS. 13A-13C) and provides sufficient extension length from the distal end of a delivery catheter or sheath to facilitate, inter alia, translation and deployment of the subject stent comprising a prosthetic heart valve as will be further discussed herein. Each attachment feature 402 is attached to a distal end of a corresponding tether assembly 410 in the manner discussed above with respect to FIGS. 7-9C.

Thus attached to the stent 100 (e.g., to the outer section 102) as described above, the tether assembly(ies) 410 may be used to collapse the expandable stent 100 into the proximal end of the lumen of a delivery catheter or sheath and assist in translating the collapsed stent 100 distally through the delivery catheter or sheath to the distal end of the delivery catheter of sheath which is pre-positioned at the heart chamber of interest. At this point, the collapsed stent 100 is at least partially released from the delivery catheter or sheath and begins to self-expand. The attached tether assembly(ies) 410 may be used to assist in this process by manipulating the tether assembly(ies) 410 to move the at least partially expanded stent 100 into proper position within the subject heart chamber. In certain cases, it may be advantageous to reposition the at least partially expanded stent 100 (which comprises a prosthetic heart valve) by pulling proximally one or more of the tether assembly(ies) 410 to move the stent 100 in a desired direction and into a desired attitude within the heart valve, relative to anatomical landmarks.

Figure 12C:
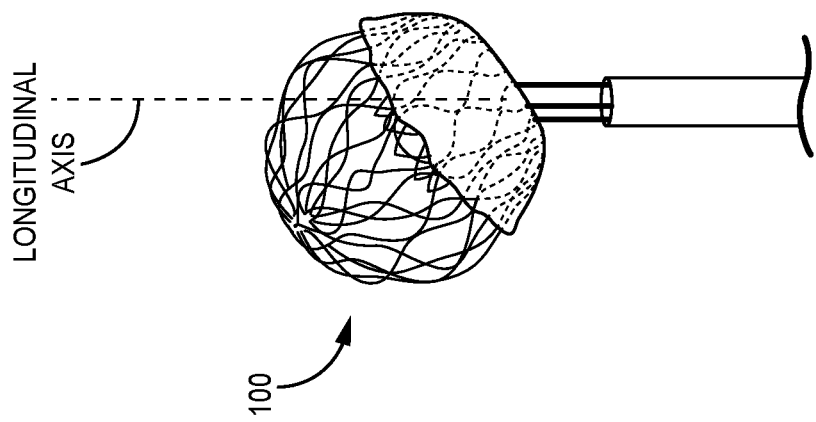
FIG. 12C illustrates three exemplary tether assemblies attached to three attachment features of an exemplary stent with displacement in a second direction relative to a longitudinal axis of a delivery catheter.
Figure 12B:
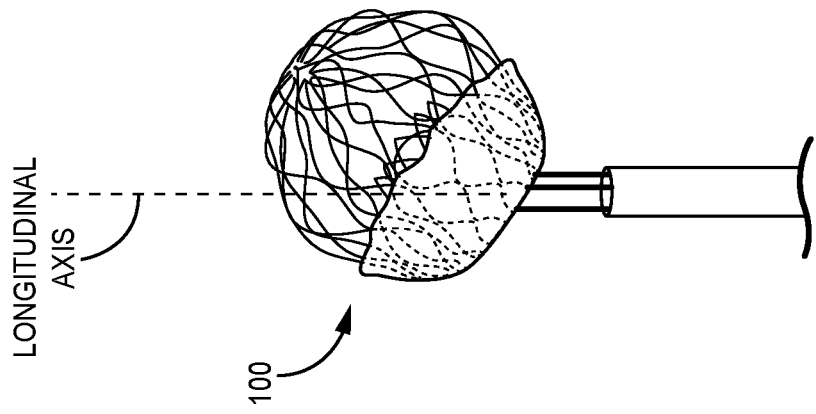
FIG. 12B illustrates three exemplary tether assemblies attached to three attachment features of an exemplary stent with displacement in a first direction relative to a longitudinal axis of a delivery catheter.
Figure 12A:
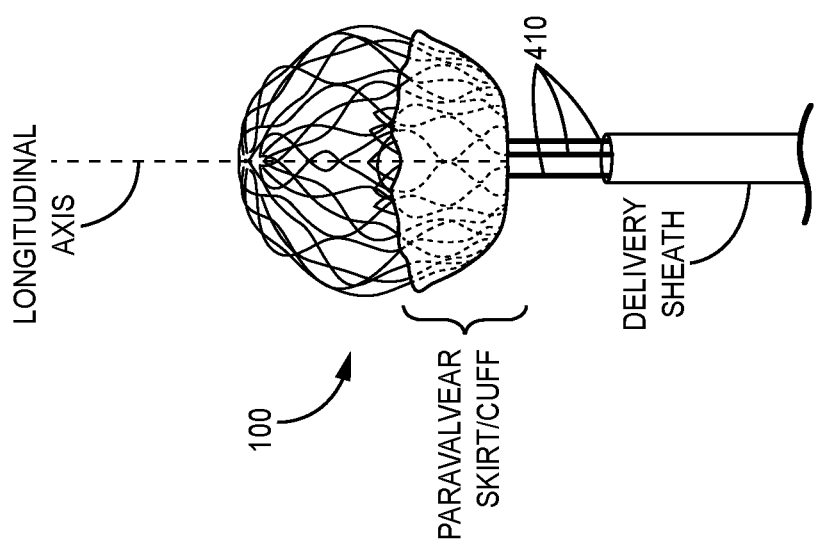
FIG. 12A illustrates three exemplary tether assemblies attached to three attachment features of an exemplary stent, without displacement of the stent from a longitudinal axis of a delivery catheter.

FIGS. 12A-12C illustrate one embodiment comprising three tether assemblies 410 wherein FIG. 12A is a default position and the stent 100 is substantially symmetrically aligned with the longitudinal axis of the delivery sheath. FIGS. 12B and 12C show the result of pulling (or pushing) one or more tether assembly(ies) 410 to cause the connected stent 100 to move away from the symmetrical alignment of the longitudinal axis of the delivery sheath to take on an asymmetrical attitude to assist in positioning and deploying the stent 100.

Figure 13A:
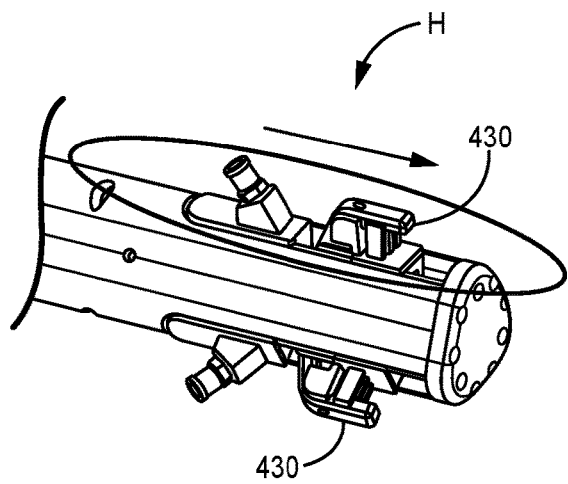
FIG. 13A illustrates an exemplary handle and mechanism for adjusting (decreasing) the extension of each tether assembly distally from the distal end of the delivery catheter or sheath.
Figure 13B:
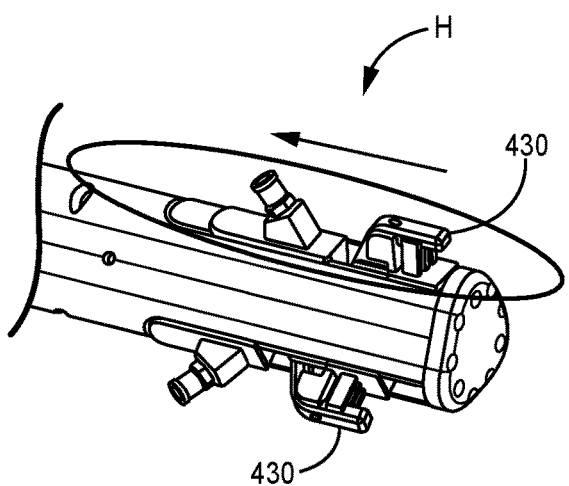
FIG. 13B illustrates an exemplary handle and mechanism for adjusting (increasing) the extension of each tether assembly distally from the distal end of the delivery catheter or sheath.
Figure 13C:
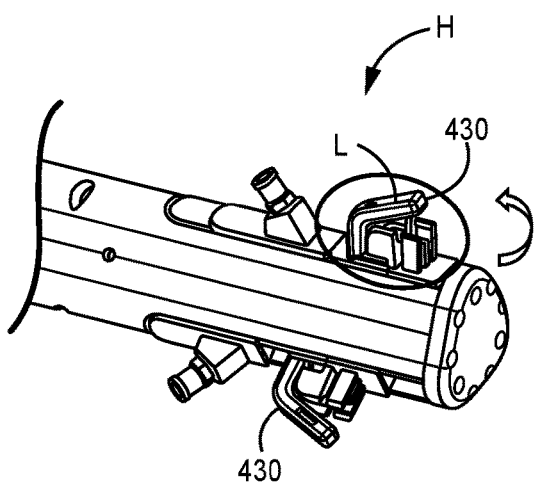
FIG. 13C illustrates an exemplary handle and mechanism for releasing one of the tether assemblies from attachment to the exemplary attachment features of the stent.

FIGS. 13A-13C provide embodiments of an operating handle H to which the proximal end of each tether assembly 410 is connected as the skilled artisan will appreciate. As indicated, the length of extension of the tether assembly 410 away from the distal end of the delivery sheath may be manipulated by moving the attached push/pull and release mechanism 430 proximally or distally at the handle H. This may be done as a combined set of tether assemblies, or individual tether assemblies 410 may be selected for selective lengthening (pushing it distally) or shortening (pulling it proximally), relative to the other tether assembly(ies) 410, and/or the components of each tether assembly 410 comprising the outer tube 404, the notched wire 408 and the attachment feature 402 with wire portion 401 and enlarged end portion 403 may each be pushed proximally and/or pulled distally independently. Each tether assembly 410 defines its own length and a release mechanism 430 attached to handle H.

Each push/pull and release mechanism 430 further comprises a lever L that may be locked and unlocked and that allows manipulation of the individual components of the tether assembly 410. When locked, the tether assembly 410 is attached to an attachment feature 402 as described above. Releasing the tether assembly 410 from the attachment feature 402 is achieved, as shown in FIGS. 13C, by unlocking the lever L by actuating it from a locked position to an unlocked position as shown, and then pulling the unlocked portion of the tether assembly 410 proximally (i.e., pulling proximally the notched wire 408 and/or outer tube 404, distally and out of attached engagement with the attachment feature 402). It will be obvious now to the skilled artisan that this same mechanism 430 may be used to advance and/or retract the components of the tether assembly 410. i.e., the outer tube 404, to achieve attachment with, and/or release from, the attachment feature 402.

In some cases, it may be advantageous to at least partially recover, resheath and/or recapture the at least partially expanded stent 100 by pulling it proximally into the lumen of the delivery catheter or sheath, then reinitiating release and deployment steps.

When the stent 100 (comprising the prosthetic heart valve) is properly positioned, the outer tube 404 is pulled proximally to expose the attachment feature 402 engaged within the notched wire 408 for disengagement or release therefrom, thereby disconnecting the tether assembly 410 from the attachment feature 402 and the stent 100. Once each provided tether assembly 410 is similarly disconnected from the stent 100, the tether assembly(ies) 410 may be withdrawn from the heart chamber.

As discussed, a preferred access route for the disclosed delivery system comprises a transapical approach, though all other delivery access routes may be successfully navigated using the disclosed invention(s).

The description of the invention and its applications as set forth herein is illustrative and is not intended to limit the scope of the invention. Features of various embodiments may be combined with other embodiments within the contemplation of this invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

We claim:

1. A delivery system for delivering an expandable prosthetic heart valve comprising a self-expanding stent frame, the delivery system comprising:
   an operating handle comprising push/pull and release mechanisms;
   three tether assemblies, wherein each of the tether assemblies is operatively connected at its distal end to a corresponding one of the push/pull and release mechanisms of the operating handle, wherein each of the tether assemblies comprises:
      an outer tube defining a lumen therethrough; and
      a notched wire configured to be slidingly received within the lumen of the outer tube and defining a T-shaped engagement channel at a distal end of the notched wire, wherein the T-shaped engagement channel is configured to be distally extended from the lumen of the outer tube; and
   the self-expanding stent frame comprising three attachment features extending from an end of the self-expanding stent frame;
   wherein:
      each T-shaped engagement channel is configured to releasably engage a corresponding one of the attachment features extending from the end of the self-expanding stent frame;
      when the corresponding attachment feature is engaged with the T-shaped engagement channel, the outer tube is configured to be advanced over the entire T-shaped engagement channel, securing the corresponding attachment feature within the engagement channel; and
      each attachment feature includes:
         a wire portion; and
         an enlarged proximal end portion having a circular shape that is configured to engage a T-shaped engagement channel corresponding to the attachment feature.

2. The delivery system of claim 1, wherein the self-expanding stent frame further comprises:
   an outer section;
   an inner valve support section extending upward within the outer section; and
   a transition cell region at the end of the self-expanding stent frame, the transition cell region extending between the outer section and the inner valve support section;
   wherein:
      the three attachment features extend away from the transition cell region of the self-expanding stent frame.

3. The delivery system of claim 1, wherein the stent frame defines a plurality of struts, and wherein each of the attachment features are defined on a corresponding lowermost downstream strut of the stent frame.

4. The delivery system of claim 1, wherein the tether assemblies are configured to be received within a lumen defined by a delivery catheter, and wherein, for each of the tether assemblies, a corresponding one of the push/pull and release mechanisms is adapted to translate a corresponding tether assembly proximally and/or distally relative to a distal end of the delivery catheter when the corresponding tether assembly is received within the lumen of the delivery catheter.

5. The delivery system of claim 4, wherein each of the push/pull and release mechanisms are adapted to selectively translate, for a corresponding tether assembly, a corresponding outer tube and notched wire relative to each other, relative to the distal end of the delivery catheter, and relative to any other one of the tether assemblies.

6. The delivery system of claim 4, wherein each of the push/pull and release mechanisms comprises a lever configured to move between a locked position and an unlocked position.

7. The delivery system of claim 1, wherein delivering the expandable prosthetic heart valve to a heart chamber treats one or more of the group consisting of: a native mitral valve, a native tricuspid valve, and a native aortic valve.

8. The delivery system of claim 7, wherein the expandable prosthetic heart valve is delivered to the heart chamber along one or more of the transcatheter access routes in the group consisting of: transapical, transfemoral, transatrial, and transseptal.

9. The delivery system of claim 1 wherein each of the tether assemblies is configured to be individually manipulated relative to other tether assemblies.

10. A method for delivering and deploying a prosthetic heart valve to a heart chamber, the method comprising:
   providing the delivery system of claim 1;
   loading and/or collapsing the expandable prosthetic heart valve into a lumen defined by a delivery catheter or sheath;

translating the collapsed prosthetic heart valve through the lumen of the delivery catheter or sheath;

delivering the expandable prosthetic heart valve into the heart chamber;

repositioning the expandable prosthetic heart valve as necessary within the heart chamber;

deploying the expandable prosthetic heart valve to, and within, the heart chamber; and withdrawing the tether assemblies from the heart chamber.

11. The method of claim 10, further comprising recapturing or resheathing the expandable prosthetic heart valve within the delivery catheter or sheath after delivering the expandable prosthetic heart valve and before withdrawing the tether assemblies from the patient, wherein recapturing or resheathing the expandable prosthetic heart valve within the delivery catheter or sheath comprises proximally moving the push/pull and release mechanisms.

12. The method of claim 10, wherein each of the push/pull and release mechanisms are adapted to selectively translate, for a corresponding tether assembly, a corresponding outer tube and notched wire relative to each other, relative to the distal end of the delivery catheter, and relative to any other one of the tether assemblies.

13. The method of claim 12, wherein each of the push/pull and release mechanisms comprises a lever configured to move between a locked position and an unlocked position, and wherein deploying the expandable prosthetic heart valve comprises releasing each of the attachment features from the corresponding T-shaped notch of the notched wire by moving the corresponding lever to the unlocked position and proximally moving the push/pull and release mechanism.

14. The method of claim 10, wherein the stent frame defines a plurality of struts, and wherein each attachment feature is defined on a corresponding one lowermost downstream strut of the stent frame.

15. The method of claim 10, wherein delivering the expandable prosthetic heart valve into the heart chamber treats one or more of the group consisting of: a native mitral valve, a native tricuspid valve, and a native aortic valve.

16. The method of claim 15, wherein the expandable prosthetic heart valve is delivered to the heart chamber along one or more of the transcatheter access routes in the group consisting of: transapical, transfemoral, transatrial, and transseptal.

* * * * *